(12) United States Patent
Medricky

(10) Patent No.: US 11,582,847 B2
(45) Date of Patent: Feb. 14, 2023

(54) LED EXTERIOR LUMINAIRE LAMP WITH CIRCADIAN ADJUSTABLE MODES

(71) Applicant: Hynek Medricky, Prague (CZ)

(72) Inventor: Hynek Medricky, Prague (CZ)

( * ) Notice: Subject to any disclaimer, the term of this patent is extended or adjusted under 35 U.S.C. 154(b) by 0 days.

(21) Appl. No.: 17/646,931

(22) Filed: Jan. 4, 2022

(65) Prior Publication Data

US 2022/0132635 A1    Apr. 28, 2022

Related U.S. Application Data

(63) Continuation-in-part of application No. 16/485,034, filed as application No. PCT/IB2018/050913 on Feb. 14, 2018, now Pat. No. 11,219,104.

(30) Foreign Application Priority Data

Feb. 15, 2017 (CZ) .................................. CZ2017-90
Feb. 14, 2018 (CZ) .................................. CZ2018-72

(51) Int. Cl.
*H05B 45/20* (2020.01)
*H05B 45/10* (2020.01)
*H05B 45/46* (2020.01)
*A61N 5/06* (2006.01)
*F21K 9/232* (2016.01)
*F21K 9/238* (2016.01)
*F21Y 115/10* (2016.01)
(Continued)

(52) U.S. Cl.
CPC ........... *H05B 45/20* (2020.01); *A61N 5/0613* (2013.01); *F21K 9/232* (2016.08); *F21K 9/238* (2016.08); *H05B 45/10* (2020.01); *H05B 45/46* (2020.01); *A61N 2005/0629* (2013.01); *A61N 2005/0652* (2013.01); *A61N 2005/0663* (2013.01); *F21Y 2105/18* (2016.08); *F21Y 2113/13* (2016.08); *F21Y 2115/10* (2016.08)

(58) Field of Classification Search
None
See application file for complete search history.

(56) References Cited

U.S. PATENT DOCUMENTS

2016/0143109 A1* 5/2016 Lal .................... F21S 6/002
                                                    362/249.02
2016/0273717 A1* 9/2016 Krames ............. G02F 1/133603

OTHER PUBLICATIONS

"International Search Report," Patent Cooperation Treaty, dated May 31, 2018.

* cited by examiner

*Primary Examiner* — Dedei K Hammond
(74) *Attorney, Agent, or Firm* — Cionca IP Law P.C.; Marin Cionca

(57) ABSTRACT

An LED exterior luminaire comprising light-emitting diodes (LEDs) with a circadian-adjustable light output mode for its medical safety comprises at least two switchable LED chip chains I and III, wherein chain I comprising at least one LED chip emitting orange light from a wavelength range of 580 nm to 610 nm and at least one LED chip emitting red light from a wavelength range of 610 nm to 700 nm, chain III comprising at least one blue LED chip overlaid with a luminophore emitting a continuous band spectrum of visible light from a wavelength range of 440 nm to 700 nm and a correlated color temperature CCT of 2200 to 4200 K, wherein chains I and III are each separately connected to a power source via a dimming ballast that regulates the proportion of input current to each chain separately.

6 Claims, 25 Drawing Sheets

(51) Int. Cl.
*F21Y 105/18* (2016.01)
*F21Y 113/13* (2016.01)

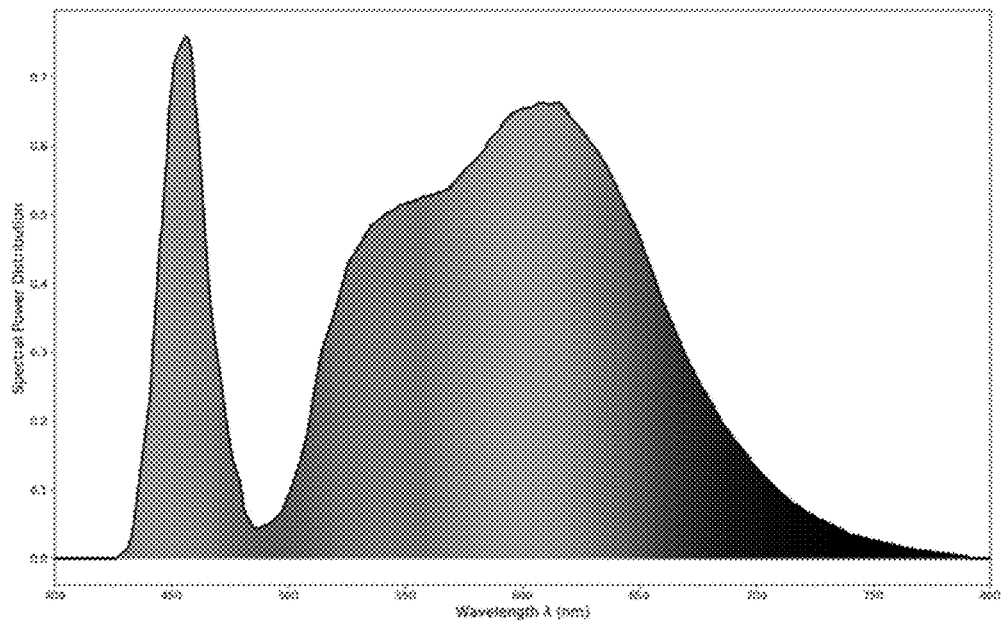

Fig. 21

| | Light source | $E_v$ [lux] | CT (CCT) [K] | CRI [%] | $E_v / E_c$ | $E_c / E_{c, HPS}$ | $E_c / E_{c, moon}$ |
|---|---|---|---|---|---|---|---|
| 1 | Sunless sky | 670 | 51 072 | irelevant | 165 % | 415 x | irelevant |
| 2 | Midday sun | 108 000 | 5250 | 99.19 | 80 % | 32 300 x | irelevant |
| 3 | Full moon | 0.02 | 4134 | 98.58 | 60 % | 0.004 x | - |
| 4 | candle | 4 | 2013 | 94.30 | 20 % | 0.3 x | 0.0022 x |
| 5 | Sodium vapor-lamp 150W | 30 | 2057 | 17.02 | 9 % | - | 204 x |
| 6 | CREE LEDway cold | 30 | 6273 | 75.02 | 77 % | 8.7 x | 1775 x |
| 7 | CREE LEDway neutral | 30 | 4466 | 80.54 | 60 % | 6.8 x | 1385 x |
| 8 | Philips LED blue | 30 | irelevant | irelevant | 580 % | 66 x | 13500 x |
| 9 | LED 2200K – warm white | 30 | 2167 | 77.85 | 18 % | 2 x | 415 x |

Properties of light sources: Ev=effective visual illumination of the horizontal plane according to $V(\lambda)$; CT=chromaticity temperature; CCT=replacement chromaticity temperature, CRI=color rendering index, Ec=effective circadian illumination according to $C(\lambda)$; Ec, HPS=ratio of effective circadian illumination of the source to the sodium lamp, Ec moon= the ratio of effective circadian illumination of the source to the moonlight

Fig. 22

LED EXTERIOR LUMINAIRE LAMP WITH CIRCADIAN ADJUSTABLE MODES

BACKGROUND OF INVENTION

1. Field of Application

The invention relates generally to LED lamps and more specifically to LED lamps having variable light level selection, and the option to elimination blue wavelengths of light according to day and night uses.

2. Description of the Related Art

More than 130 years ago, people were going to bed after sunset without being affected by any artificial lighting. However, with the invention of bulb, the bedtime shifted with the day being forcibly prolonged, leading to insomnia rise in a large number of people.

The first bulbs' filaments were formed by charred bamboo strings or threads giving light similar or equal to fire light, i.e. red monochromatic light without the blue wavelength. Later on, tungsten began to be used as the most suitable material and it is currently still used. Light emitted by a tungsten source already contains the blue wavelength. LED sources are the latest ones which use a blue LED to emit light in the shorter wavelength spectrum or create white light using RGB chips, i.e. by mixing three basic colors. In addition to these light sources, LED TV sets, mobile phones, tablets etc. appeared progressively in the market. They emit blue light to the eyes all day, even after the sunset.

The population generally does not feel the arising issue of blue light emission consciously, but this is perceived by photosensitive retinal ganglion cells. These cells influence the circadian rhythm that tells the body what time it is. The key role in synchronizing the internal biological clock is played by the hormone melatonin, the creation of which is conditioned by full darkness. In addition to sleep control, melatonin has preventive effects against cancer, slowing down aging, and helping to prevent Alzheimer's and/or Parkinson's disease. Melatonin levels are reduced during night work shifts or, for example, if a person wakes up in the middle of the night and turns on a device that emits a blue wavelength light. The boundary at which light does not influence melatonin levels is above 600 nm which is the red color wavelength. Thus, light sources with a high blue color proportion, with a wavelength around 460 nm, should generally not occur at night. However, these wavelengths of light may still be present in such rooms where human attention is needed, such as in operating theaters, flight operations, and so on. However, in many situations, people may not need a daylight replacement or exact color recognition at night, but instead it may be sufficient to see by a reddish light color. The solution could be in using electronic devices with red glasses or a red filter applied after 2100 hours. So far, either fire or a tungsten filament bulb dimmed with a dimmer was a suitable light source to be used after 2100 hours in a household. (MEDŘICKÝ, Hynek. *Light and its impact on human body*. Light. 2015, 2015(6), 53-57.)

Today, more than 60% of the population lives in environments with night light pollution. The illumination levels in urbanized areas typically reach levels around 20-80 lux, however, even values exceeding 100 lux are no exception which is a thousandfold of the full moon's light intensity. The high ratio of the blue spectrum color may have a negative impact on the human sleep quality in neighboring objects or even on the life cycles of animals, mainly the birds. The human organism can then falsely perceive light as a day signal in the middle of night, triggering biochemical processes to secureits daily activity, thus supporting its exhaustion (Burnett D. (2015) *First do not harm: Practicing lighting design or medicine . . . without licence*? Lecture at 6th Velux symposium, London.).

Light pollution is easy to find at a glance when we look up to the sky and we cannot see the stars. The more blue wavelength is present, the more light pollution is present. Currently, there are few people using low pressure sodium lamps (LPS) but these have faded away after entry of LED lamps. These lamps do not provide any blue wavelength, they emit just monochromatic amber-yellow light, and thus they have the least environmental impact and least affect circadian rhythms. They are utilised in astronomical observatories and for nesting of sea turtles. Narrow-band amber LED extends the orange-yellow wavelengths with the green one and they are not so safe. So-called PC amber LED covers all the green wavelength range. In municipality Santa Pau in Garrotxa Region, street LED lamps have been replaced with PC amber LED lamps, and the latter partly eliminate the blue wavelength, the light is then much more pleasant in the evening but blue wavelengths are not eliminated completely. Another LED type is a filtered warm white LED-straw yellow LED lamp with a filter that removes most emission with wavelength below 500 nanometers. Another type of a LED, which is almost neglected, is a warm-white LED with chromaticity temperature of 2700 K. The most frequently used LED is a cold LED with chromaticity temperature about 5000 K or 4000 K. This source of light that covers all the spectrum is misused in household and in street lighting day and night. (A comparison of the representatives of lamps and their spectra is presented in FIG. 1) (http://www.flagstaffdarkskies.org/for-wonks/lamp-spectrum-light-pollution/).

The LED activity principle is based on radiating energy in form of photons while electric current is passing through a semiconductor junction formed by semiconductormaterial, typically GaN or InGaN. Overview of application of semiconductors in current colour LEDs:

Infrared—$\lambda > 760$ nm, gallium arsenide (GaAs), aluminium gallium arsenide (AlGaAs)Red—$610 < \lambda < 760$ nm, aluminium gallium arsenide (AlGaAs), gallium arsenide phosphide (GaAsP), aluminium gallium indium phosphide (AlGaInP), gallium phosphide (GaP).

Amber—$590 < \lambda < 610$ nm, gallium arsenide phosphide (GaAsP), aluminium gallium indium phosphide (AlGaInP), gallium phosphide (GaP)

Yellow–$570 < \lambda < 590$ nm, gallium arsenide phosphide (GaAsP), aluminium gallium indium phosphide (AlGaInP), gallium phosphide (GaP)

Green–$500 < \lambda < 570$ nm, aluminium gallium indium phosphide (AlGaInP), gallium phosphide (GaP), aluminium gallium (AlGa), aluminium phosphide (AlP)

Blue—$450 < \lambda < 500$ nm, zinc selenide (ZnSe), indium gallium nitride (InGaN), silicon carbide (SiC)

Violet—$450 < \lambda < 500$ nm, indium gallium nitride (InGaN)

sUltraviolet—$\lambda < 400$ nm, aluminium nitride (AlN), aluminium gallium nitride (AlGaN), aluminium gallium indium nitride (AlGaInN)

Any LED emits colour spectrum according to the applied semiconductor. LEDs, however, cannot emit white light because white light is a mixture of all colours. Photoluminescence is used to produce white light. Luminescence occurs when an atom is excited through action of other radiation, electrons and the like, and then the atom returns in its ground state and a photon is emitted. The substances where the luminescence occurs are called luminophores. LEDs are fitted with a thin layer of luminophores embedded in a silicone mixture, it is favourable to use a mixture of several different luminophores according to the required resulting colour spectrum.

The most important LED properties are these: chromaticity temperature and colour rendering index. Chromaticity temperature is given in Kelvin (K) and it represents the colour rendering of light. The more kelvins a Led has, the more the artificial light resembles day sun light. Classic bulbs have this value around 3000 K, white cold LED has about 5000 K which is close to day bright light. Chromaticity temperature of household lamps should differ according to their application (higher chromaticity temperature in kitchen than in bedroom).

Another important property is the colour rendering index (CRI) which determines ability of a light source to reproduce colours of an illuminated object when compared with natural sunlight. The ideal value is 100 which corresponds to the day sunlight, most frequently used LED lamps have CRI about 80. The above mentioned sodium lamps have zero colour rendering (CRI=0) and thus this lamp is not advised to use, e.g. during winter when the dark comes at 5 p.m. but we still need to work and to distinguish colours. White light without using luminophores is used through a so called RGB LED where blue, green and red chips are switched together. The colour rendering index is, however, rather bad, it is about CRI=24.

The key function of melatonin in a man is regulation of the circadian regime of an organism. Melatonin is therefore primarily a chrono-biotic substance (Illnerová, H. 2008). If we spend a day in a cyclic manner, we have the day divided, without always realising this precisely, into a subjective day and a subjective night. When our subjective night is approaching, we begin to feel sleepy. Hormone melatonin starts to create in epiphysis situated in brain and it starts to discharge in blood. Melatonin expands vessels in our limbs, our warm escapes in environment and body temperature drops. Generation of melatonin drops or stops completely early in the morning and temperature rises. Also generation and release of hormone cortisol from adrenal glandsrises" (FIG. 26) (Illnerová, H. 2005, p. 9). It is a hormone which is discharged under stress the task of which is to pre-prepare us to troubles of the coming day. Of course, there are many other changes before the daybreak. The most important thing is to get up when our body is ready for the day (Illnerová, H. 2005, p. 9-10).

On the other hand, we can increase the production of melatonin by exposure to sunlight over the day. The sunlight also has positive effects against depression. On the other hand, absolute dark must be at night when sleeping (Tab. 2) (Fořt, P. 2008).

Response of melatonin production to wavelength light from 440 to 600 nm has been tested with volunteers. It was found that is it necessary to decrease the light wavelength to 420 nm. Sensitivity to this wavelength has been tested with several volunteers placed in a dark room. Half of the volunteers was exposed to wavelength light of 420 nm from 2:00 till 3:30, and the other half stayed in dark. First half of volunteers, exposed to light radiation, the melatonin level dropped to 76.4 or 47.6 pg/ml. Second half the melatonin level ranged around 70 µg/ml. The volunteers who were exposed to wavelength 420 nm had melatonin level decreased by six orders. It was found that the most efficient range of wavelengths for melatonin regulation is 446-477 nm (FIG. 2) (BRAINARD G C, et al.). Action Spectrum for Melatonin Regulation in Humans: Evidence for a Novel Circadian Photoreceptor. *J Neurosci*. 2001, Aug. 15; 21(16): 6405-12.).

There are many manufacturers of LED lamps but they do not address elimination of the blue light which effect is not healthy for a man at night. When assessing current light sources with some possibility to be switched, with transition phases and the like, we can find that if some technical solutions have addressed "safety", it concerned primarily protection of the source, of the technical system or of the property, etc. The presented concept, however, considers the "safe" mode of the light source in a quite different and new relation of a long-term effect on human health.

Because of European effort to decrease power consumption, there is still the option to provide for lighting using dimmed halogen bulbs in interior spaces and using sodium bulbs in outside spaces late evening and at night but awareness of economy of LED sources spreads and it results in general preference at the expense of the current sources, input of which before dimming discourages a consumer. Corruption of circadian rhythms and particularly of night immune and regenerative processes of inhabitants and of whole ecosystems living next to human residences and communications have not been addressed, yet.

Conception—Basic Idea

In common interior and exterior illumination practice, we have been using artificial light sources from more than 100 years and they are typically designed with just one mode of emitted light. However, life on earth has taken place in the natural conditions of variable illumination character for millions of years which may be also one of the fundamental prerequisites for live nature functioning as we know it—day and night changing. Scientific research of recent years show that the influence of the so called"modern" light sources on the human population health has been strongly underestimated so far. Economic focus of the industrial civilizations as a result of the mass use of light sources to "prolong the day or the time during which one can work" significantly affects the natural night conditions that have meant the sleep mode for a human, while this is a summary of several properties of the light being used, not just a single parameter like illumination intensity etc. The presented concept brings the extension of the current light sources with the products working in several operating modes focused on ergonomics and health impacts on the operator mainly in the areas of affecting the sleep mode.

Input Conditions and Requirements

Scientific studies prove that the creatures' organisms are accustomed to a certain course of light character changes during the day phases in the long-term development, while the so called "biological clock" of live organisms and obviously a human also follow such changes to a large extent. The light sources being so far in mass production are primarily designed to provide spare daylight for example in enclosed spaces or "artificial day prolongation" till evening and night hours. Such light is suitable provided that it's used to illuminate a human activity traditionally performed in daylight (such as work, sport, study). Obviously, it's no more fit for other phases that are typical for the course of the day and vital for health—these include evening relaxation phase (attenuation and natural daylight changes before the sunset) as well as the sleep preparation phase which was accompanied in the long term by staying in environment slightly lit by fire. The technical specifications provided by the scientific research also show which visible spectrum bands are important for healthy and natural course of the above-mentioned phases of relaxations and sleep preparation:

a) critical blue band—typically 440-470 nm
causes the internal "wake-up" of organism and prevents the sleep preparation b) white-green band of brightness—typically 520-575 nm
within this band, we are most sensitive as regards the brightness and such illumination helps us to stay in active mode c) amber band—typically 585-610 nm
this is the area of light optimal for the evening relaxation phase and this is where the"safe" band for possible sleep preparation begins d) red band—typically 610-700 nm
this is quite safe for the night sleep phase and in addition, as the human vision brightness sensitivity starts to decrease sharply, such illumination is virtually perceived as being just "very weak"

BRIEF INVENTION SUMMARY

Application in Industry
A light source suitable in households and public lighting that can be switched between three modes, where the first mode completely eliminates blue wavelengths and does not disturb circadian rhythms in humans and animals.

Subject Matter of the Invention
A quite new lamp has been developed that concentrates on harmonisation of circadian rhythms of men and animals, thus of all beings affected by the modern way of life concerning light pollution. It has shifted the effect required of light to conform to the day rhythm of a man, thus of circadian rhythms on a day and, on the other hand, it has suppressed undesirable imbalance of these rhythms at night when we need to see and to make light.

LED lighting consists of two, at least, extreme light sources, namely for the day mode and for the night mode. The night lighting mode is provided just with the red and amber light with parameters like a fire has, and the day mode is provided with blue LEDs covered with luminophores with parameters similar to sunlight on a bright day. The night lighting mode emits monochromatic red and amber light with wavelength about 580 to 680 nm only.

It is favourable to have the night mode light emitted from a LED chip monochromatic with maximum at 590 nm for amber light and maximum at 628 nm for red light. The unusual direct red and amber light without any excitation in blue wavelengths has been used in the night mode to be completely sure that light radiation from these LED chips contains no blue and green light which would imbalance an organism and wake it from the night mode.

Thus, it is possible to have the LED light in the night mode for easy short-term use, for example when one awakes and needs to go to the bathroom or for all the night when nursing a baby without the user being harmed by feeling of sleeplessness, even in the short term.

In some embodiments, provided herein is an exterior luminaire comprising light-emitting diodes (LEDs) for emitting light, with a circadian-adjustable light output mode for medical safety, comprising at least two switchable LED chip comprising a chain I and a chain III, wherein the chain I comprises:
a first LED chip emitting orange light having a wavelength range of 580 nm to 610 nm, and
a second LED chip emitting red light having a wavelength range of 610 nm to 700 nm, wherein the chain III comprises:
at least one blue LED chip overlaid with a luminophore emitting a continuous band spectrum of visible white light having a wavelength range of 440 nm to 700 nm and a correlated color temperature CCT of about 2200 to 4200 K, wherein the chains I and III are each separately connected to a power source via a dimming ballast that regulates a proportion of an input current to each chain separately, such that switching between the chain I and the chain III is accomplished via a switching interval that is set for a period of at least 3 minutes, wherein the change in the input current occurs at a maximum rate of 25% per 1 minute, wherein the proportion of the input current to each chain changes by the value to one chain decreasing and the value to the other chain increasing.

In some embodiments, the switchover from the chain I and to the chain III is set to at least 30 minutes, wherein the change in the input current occurs at a maximum rate of 2.5% per 1 minute. In some embodiments, the switchover from the chain I and the chain III is set to at least 60 minutes, wherein the change in the input current occurs at a maximum rate of 1.5% per 1 minute. In some embodiments, the dimming ballast is controlled by software or via a protocol. In some embodiments, the correlated color temperature CCT of the at least one blue LED chip is about 2500 to 2800 K. In some embodiments, the color rendering index (CRI) of the emitted light has a value of at least 80.

BRIEF DESCRIPTION OF THE DRAWINGS

For exemplification purposes, and not for limitation purposes, aspects, embodiments or examples of the invention are illustrated in the figures of the accompanying drawings, in which:

FIG. 16: Block scheme related to Example 8a.
FIG. 17: Block scheme related to Example 8b.
FIG. 18: Block scheme related to Example 8c.
FIG. 21: Spectrum of luminophore with blue LED for 4000 K—III. chain, produced according to Example 3b.
FIG. 22: Properties of light sources—state of the art

DETAILED DESCRIPTION

Figure 1:
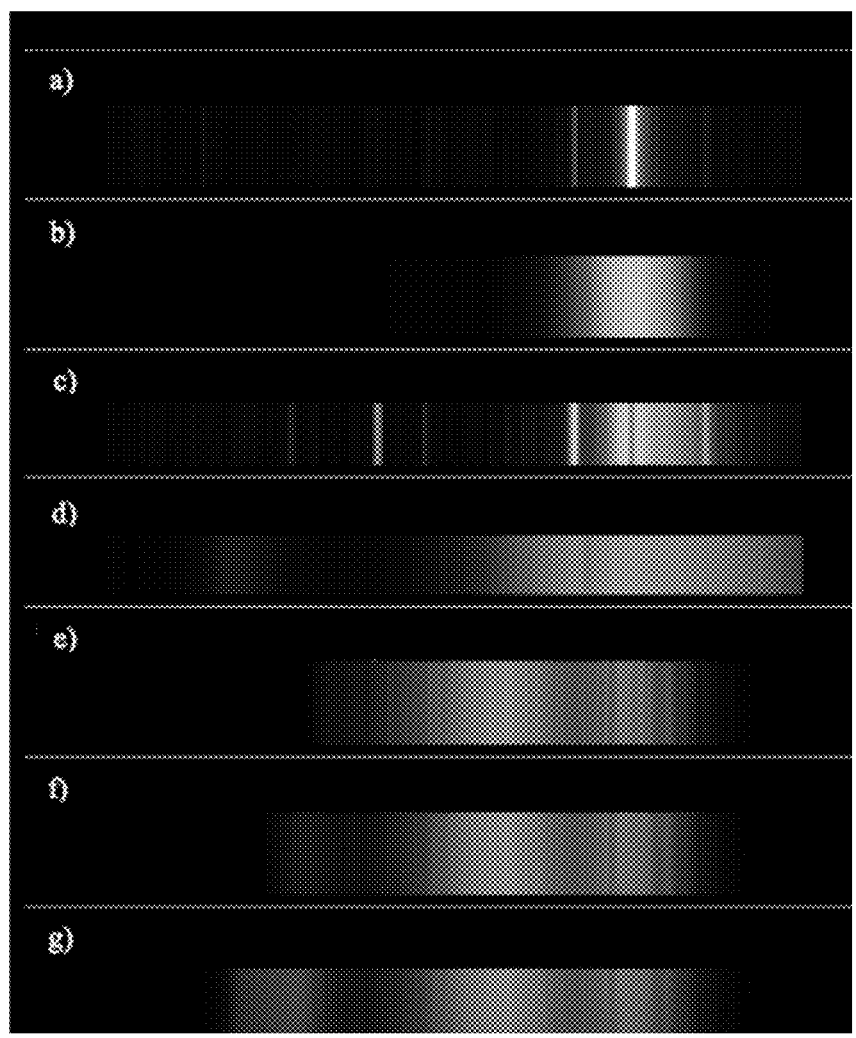
FIG. 1: Comparison of representative light sources and their spectra according to the state of the art: a) low pressure sodium lamp, b) monochromatic LED with semiconductor AlInGaP with wavelength 590 nm to 595 nm, c) high pressure sodium lamp, d) PC amber, e) filtered warm white LED, f) cold white LED with chromaticity temperature of 4100 K, g) cold white LED with chromaticity temperature of 5100 K.
Figure 2:
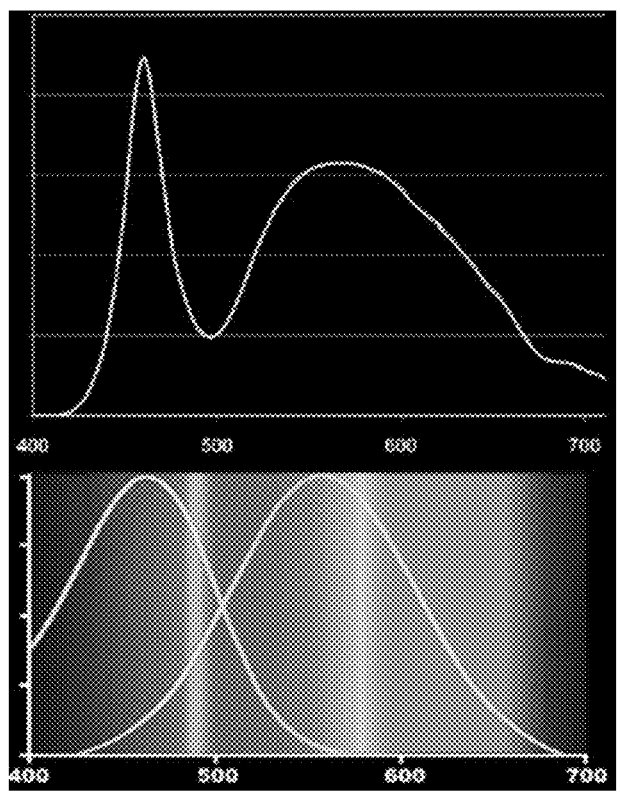
FIG. 2: Sensitivity to light wavelength: spectrum of common white LED with colour temperature 4800K (above). The left curve in the lower figure shows sensitivity of melatonin and the middle curve shows sensitivity of human eye in standard day vision.
Figure 3:
FIG. 3: Unsuitable source of light LED 3098 K—little blue wavelength for work, too much blue wavelength for relaxation.
Figure 4:
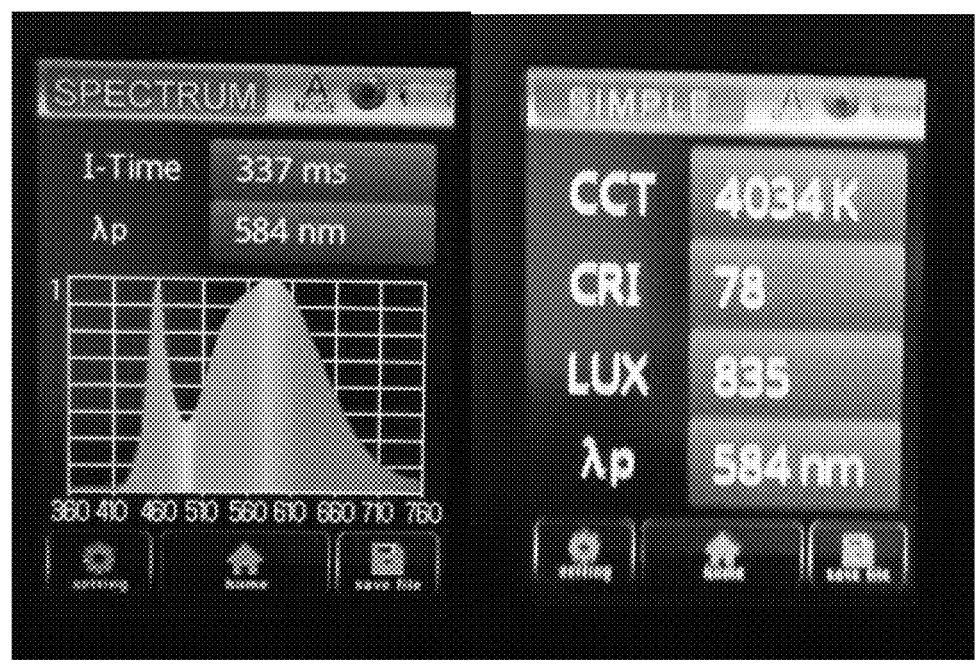
FIG. 4: Commercial LED bulb 4034 K with low CRI value
Figure 5:
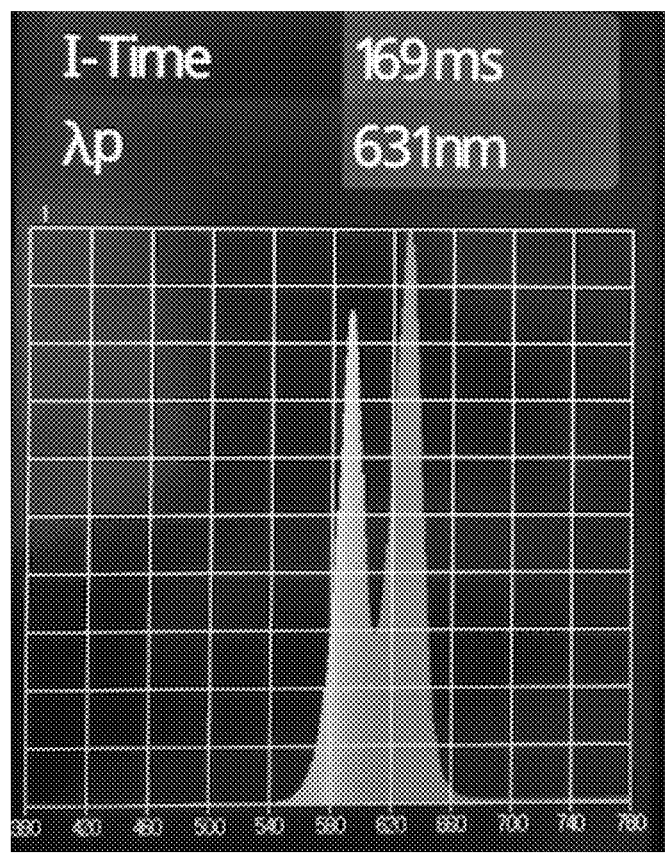
FIG. 5: I. chain of LED lamp: amber:red 4:5
Figure 6:
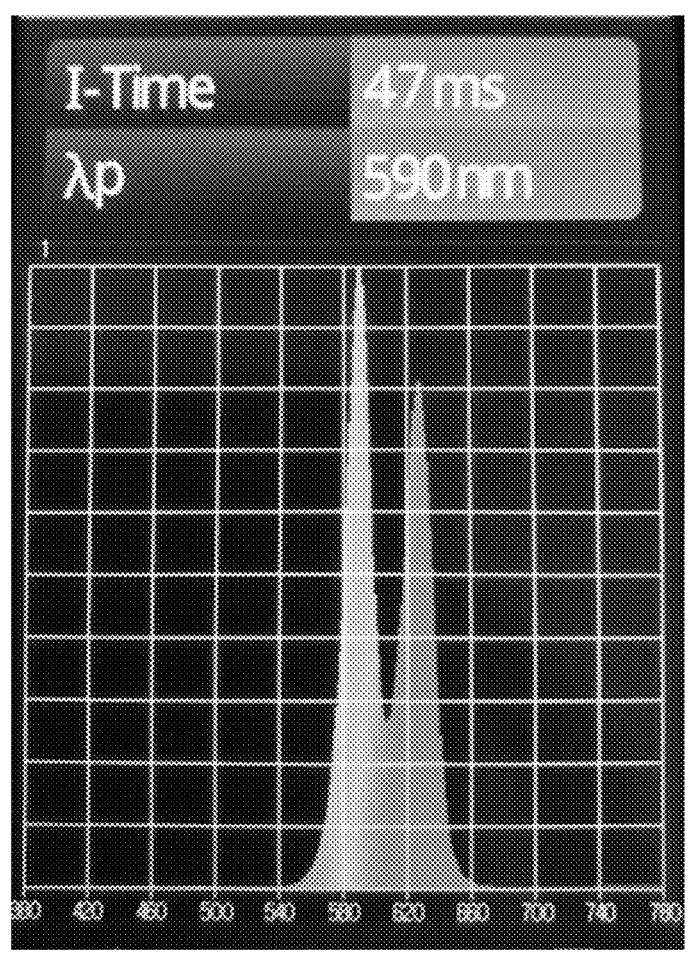
FIG. 6: I. chain of LED lamp: amber:red 6:4
Figure 7:
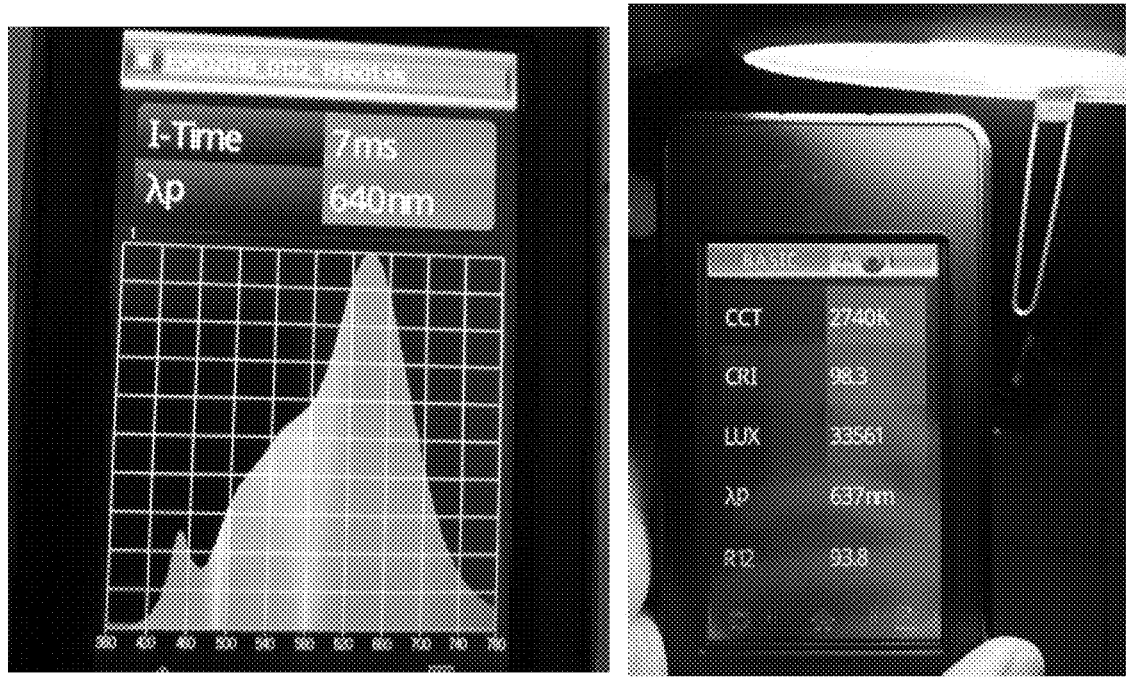
FIG. 7: II. chain of LED lamp: CRI=98.3, blue 15%, green 25%, red 60%
Figure 8:
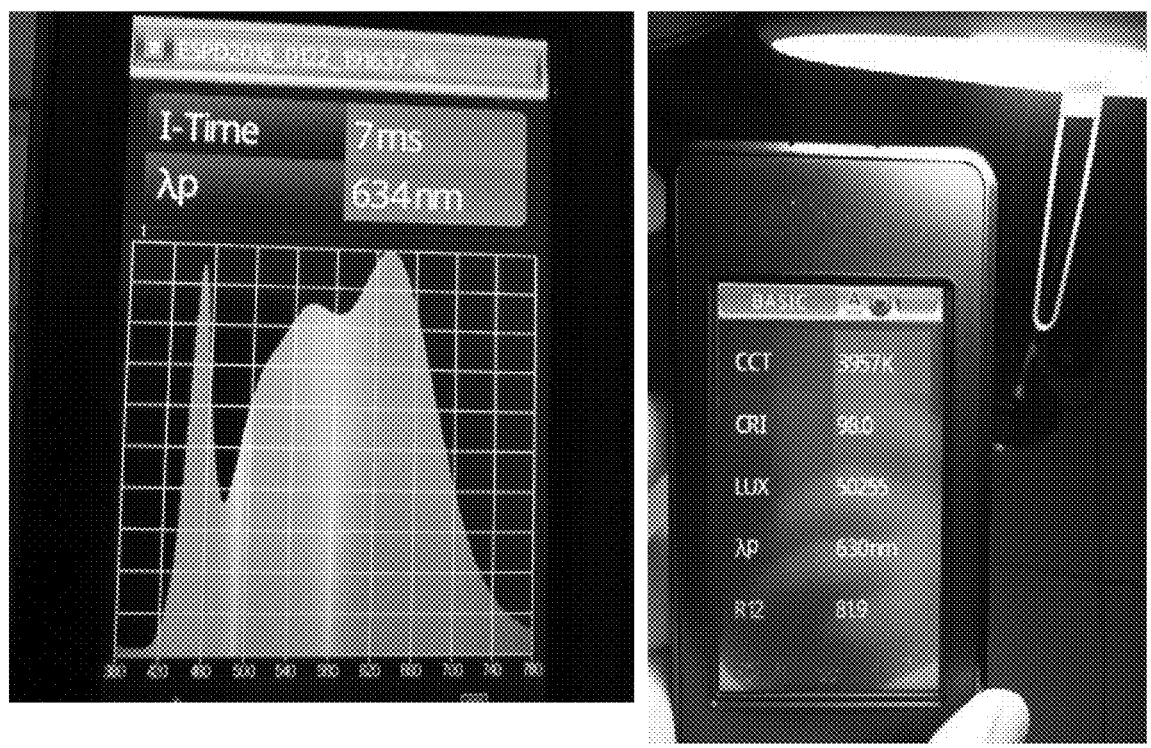
FIG. 8: III. chain of LED lamp: CRI=98, blue 25%, green 35%, red 40%
Figure 9:
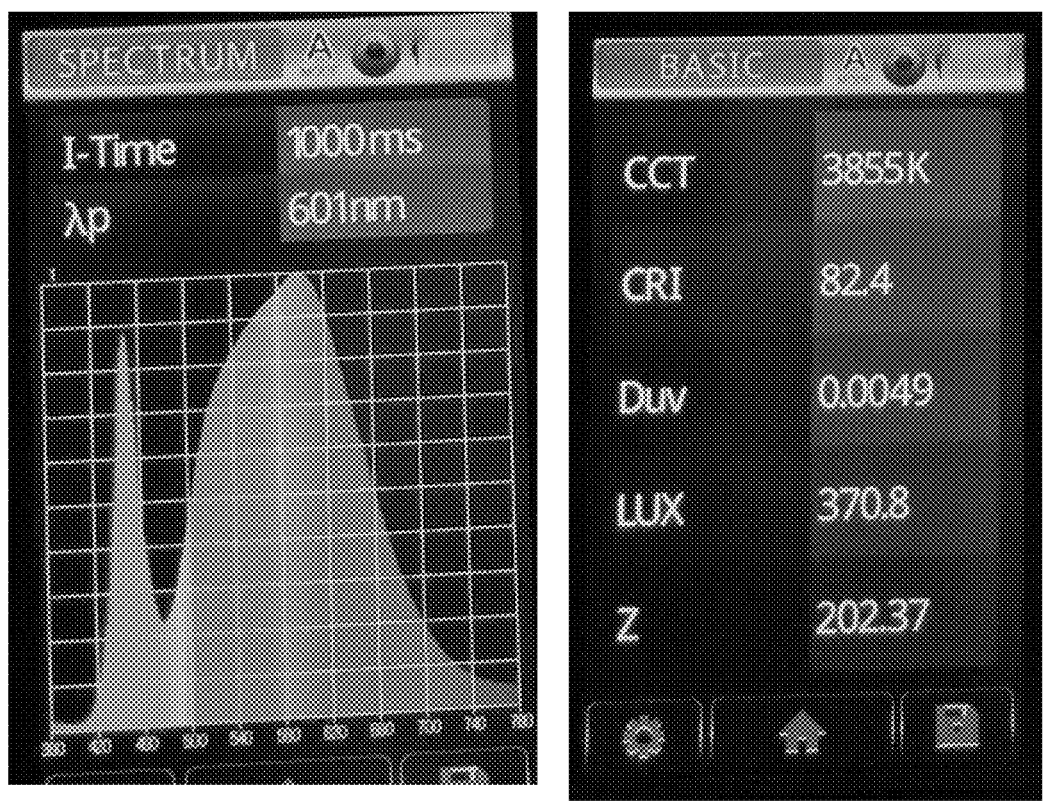
FIG. 9: Outside lamp—III. chain
Figure 10:
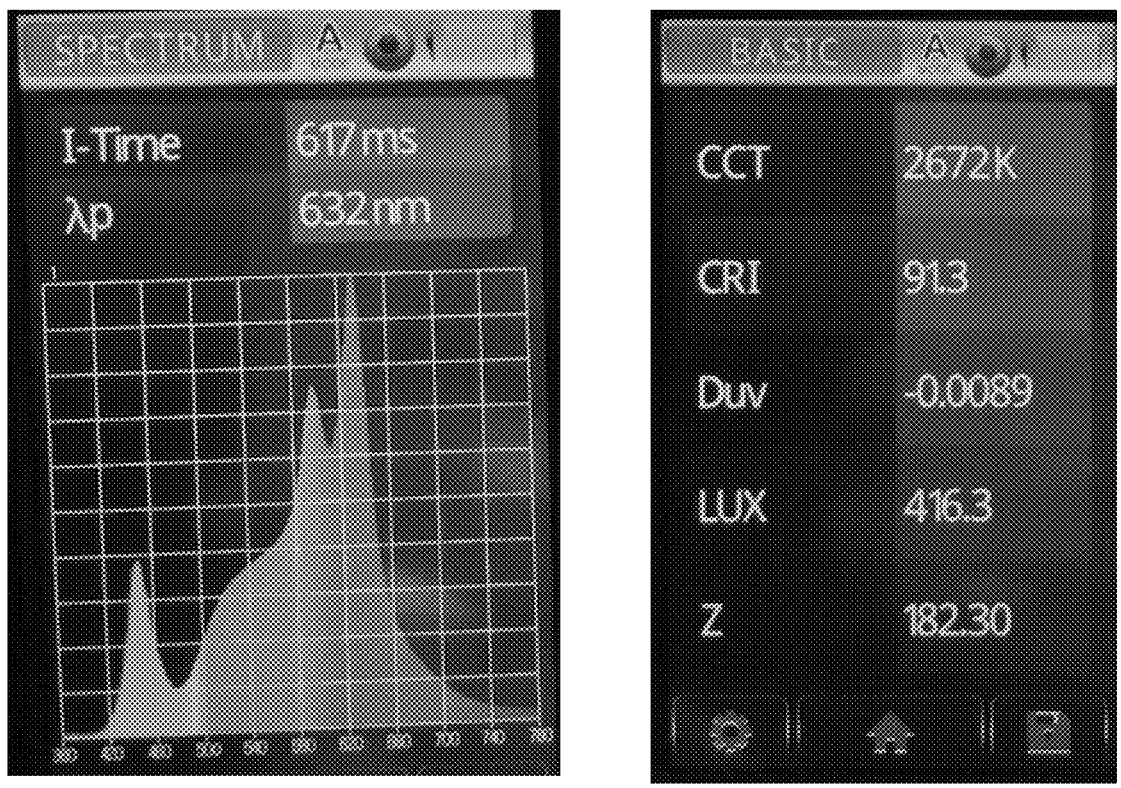
FIG. 10: Outside lamp—combination of I. and III. chain
Figure 11:
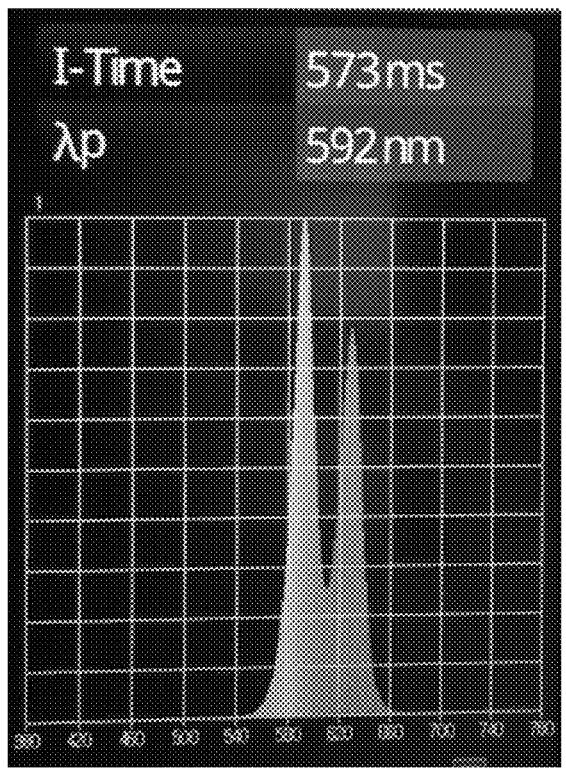
FIG. 11: Outside lamp spectrum—I. chain, amber:red 3:7
Figure 12:
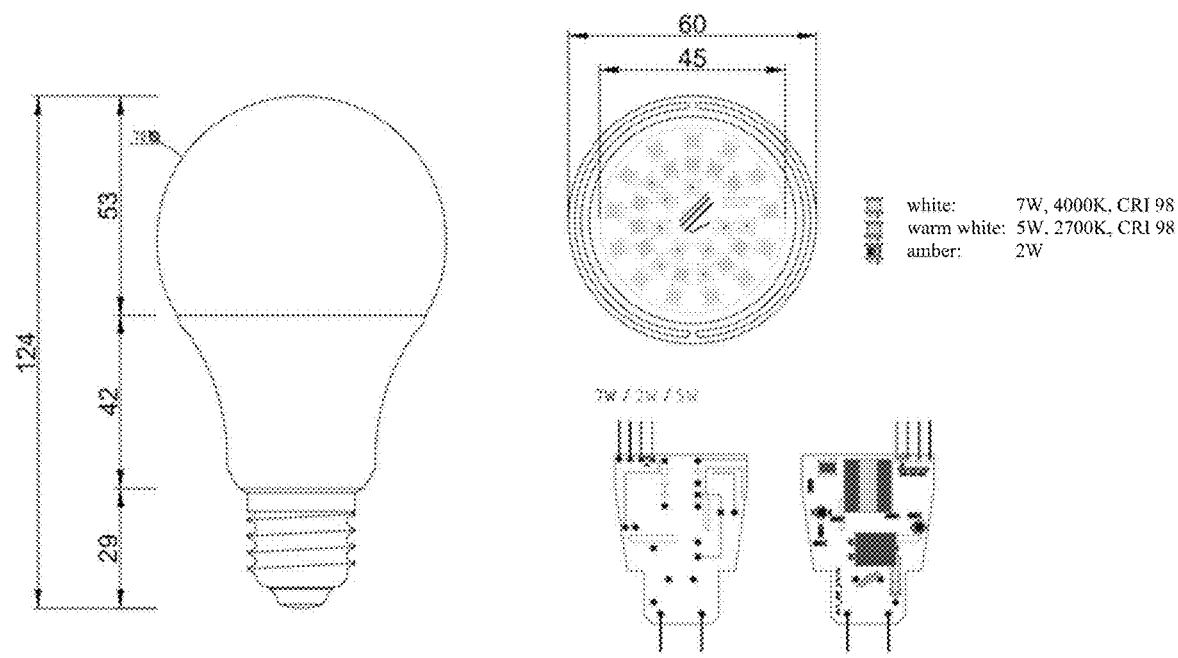
FIG. 12: Schematic drawing of inside LED lamp with manual switch
Figure 13:
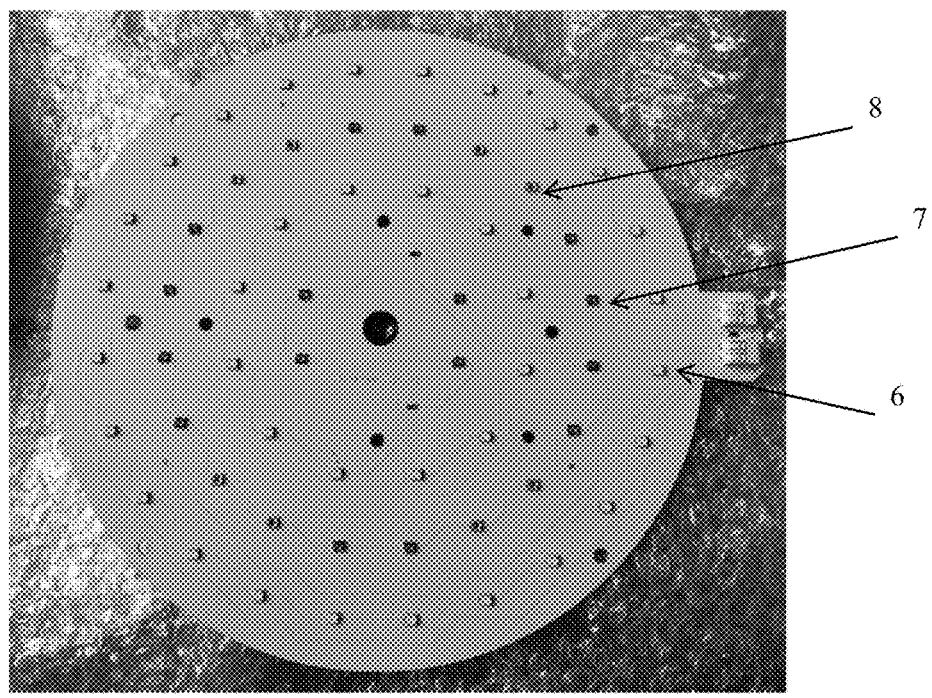
FIG. 13: Ceramic plate with chips for an outside lamp

A LED lamp is connected in such a way that the first switch always starts the night mode under the manual control. So a sleepy user need not solve what and how to switch at night without risking being exposed to the daylight by mistake. The day lighting mode would only occur within further switching. Amber light is satisfactory for safe not-waking lighting but addition of red light would cause a more pleasant feeling.

The day lighting mode is provided by blue LED chips covered with luminophores emitting continuous band spectrum of visible light with wavelength 380 nm to 700 nm and chromaticity temperature CCT 3500 to 4200 K, it is favourable to have the CRI 90 value or more which provides for high fidelity of colour rendering and the light spectrum is similar to that of a bright day. Under such lighting an organism is more excited and a brain is stimulated to higher cognitive performance. The difference against common bulbs is similar to light on a rainy or a sunny day when a man is a bit more alert than in rain.

Thus a LED lamp consists of light emitting diodes (LED) with circadian regulable mode of radiated light providing for its health safety because is contains two, at least, switchable chains of LED chips. I chain for the night mode and III chain for the day mode and the I. chain contains one, at least, LED chip emitting amber light in range of wavelength 580 nm to 610 nm and one, at least, LED chip emitting red light in range of wavelength 610 nm to 700 nm, III chain contains one, at least, LED chip covered with luminophore emitting continuous band spectrum of visible light of wavelength 440 nm to 700 nm and chromaticity temperature CCT 3800 to 4200 K. It is favourable, if the emitted visible spectrum of the III chain consists of relative share of 25 to 33% of blue colour, 22 to 35% of green colour and 38 to 45% of red colour.

It is favourable if a LED lamp also contains an evening lighting mode which emits continuous band spectrum of visible light with wavelength 380 nm to 750 nm and chromaticity temperature CCT 2500 to 2800 K and it is favourable if its colour rendering index CRI has value of 80, at least.

The evening lighting mode serves for preparation for sleep and for relaxation, the emitted light contains low share of blue colour and it is similar to day light 45 minutes before sunset.

The evening lighting mode js provided either with a II. chain of LED chips which contains one, at least, blue LED chip covered with luminophore with chromaticity temperature of CCT 2500 to 2800 K or it is mixed through switching the I. and the III. chain together with the possibility to apply variable intensity of each chain and continuous or gradual transition into the night lighting mode and lighting of only the I. chain. It is favourable if the gradual or continuous transition between the lighting modes is provided by insertion of a dimmer between the chains.

The evening lighting mode emits visible spectrum consisting of relative share of 7 to 19% of blue colour, 27 to 31% of green colour and 50 to 65% of red colour.

The spectral maxima of light intensity according to light wavelength were used to determine the ratios among the represented spectrum colours as follows: blue spectrum colour—maximum at 455 nm, green colour—maximum at 555 nm and red colour—maximum at 628 nm.

A LED chip consists of compound semiconductors. A characteristic semiconductor applicable for a blue LED is:
  a) Indium gallium nitride (InGaN) which is used for shorter wavelengths, i.e. for the light connected to daily activities and we consider this alloy to be fully unwanted for the relaxation/sleep mode.
  Gallium is a necessary element for application in band about 580 nm and higher. Other elements can be added to modify the band emitted.
  b) Aluminium gallium indium phosphide (AlGaInP) which occurs in the production of relatively widespread red-amber LED elements and meets the requirements for the "safe" band for relaxation/sleep preparation
  c) Gallium arsenide (GaAs) is a typical material for pure red light on the edge of the visible spectrum, thus being quite safe even for the night sleep mode.

Blue LEDs are coated with luminophores. It is favourable to use luminophores with commercial name ZYP630G3, emitting maximum light at wavelength of 628 nm and ZYP555G3, emitting maximum light at wavelength of 555 nm that have been dispersed in a silicone bed that was applied over the blue LED. The bed for the LED can be of various shape, it is favourable to have a wall of the LED bed inclined by 20° against level.

The II. chain (evening mode) has been designed in such a way that the outgoing light which passes from a LED through luminophore consists of 30% blue, 20% green and 50% red colour of the light spectrum. The III. chain (night mode) of lighting has been designed in such a way that the outgoing light which passes from a LED through luminophore consists of 50% blue, 20% green and 30% red colour of the light spectrum.

The night mode completely eliminates light blue wavelength the action of which harm human organism at night. It is advisable to switch on this light everywhere after 9 p.m., and to use it till sunrise. The evening mode has blue wavelength and it is advisable to see it in the afternoon and for reading. The day mode represents the full day sunlight and it should only be used during a day from sunrise till dark, both home and in offices, and possibly in circumstances where vigilance and performance are required.

The manual switching of chains is set so that after lights are switched off and on again, first the I. chain is switched on with monochromatic amber and red colours, thus no effect on circadian rhythm and sleep quality would occur after each wake and switching light on. The switching works in such a way that a filtering capacitor is charged to 5 V, and it starts discharging after the light is off or power supply is off. If voltage drops under 2 V, on the next light switching-on the I. chain with monochromatic amber and red colours switches on, this occurs after some 10 seconds. If the light is switched in shorter time, the capacitor is discharged to, say, only 4 V, the system will not switch automatically into the I. chain but into the next chain.

Values of colour rendering index are for the II. and III. chains 80 or more, thus they almost correspond to the natural sunlight.

A light source with switch into the "safe" light mode for an observer
 a) critical blue band—typically 440-470 nm
  causes the internal "wake-up" of organism and prevents the sleep preparation
 b) white-green band of brightness—typically 520-575 nm
  within this band, we are most sensitive as regards the brightness and such illumination helps us to stay in active mode
 c) amber band—typically 585-610 nm
  this is the area of light optimal for the evening relaxation phase and this is where the"safe" band for possible sleep preparation begins
 d) red band—typically 610-700 nm
  this is quite safe for the night sleep phase and in addition, as the human vision brightness sensitivity starts to decrease sharply, such illumination is virtually perceived as being just "very weak"

Thus, the proposed conception of a light source assumes that at least one of the operating modes will be quite free of energy in the critical blue band a) or attenuated by several orders of magnitude with respect to the major band c) or d).

Switching or gradual transition to the safe mode for relaxation/sleep may happen in several manners:
 a) in automated mode
  based on the coordination for example with a sensor of natural light brightness or any sophisticated control system
 b) direct switching by user
  in this case, this concept assumes that the "safe mode" should be the first one in which the source begins to light after being enabled from the off state.

An Inside Lamp of DEN Type (Day, Evening, Night)

In the time from dusk, which for example occurs in December around 4 p.m., till evening, the source operates in the Day Mode and it completely emits short wave photons, like the sun during a day in summer. Evening, the source switches automatically or manually into the Evening Mode where it emits markedly less short wave photons and more long wave ones which simulates a situation before sunset. Then, at 9 p.m., thus 90 minutes before the usual time for going to bed (when traffic drops), the DEN source switches into the Night Mode, where it emits light completely without short wavelengths and thus it does not disturb the circadian rhythms. Taking into account that 65% cones in human eye catch long-wave photons, 33% cones serve to catch the medium range and only 2% cones provide for vision in the short-wave range, the switch to the long-wave light will not harm vision, the opposite is true, markedly less long-wave photons (of red and amber light) satisfy for adequate visual orientation, than for short-wave light (blue, green). Early morning, a LED lamp switches first in the Evening Mode and then into the Day Mode where it stays till full day.

Exterior Luminaire

In the time from sunset till late evening a lamp operates in the Day Mode and it emits high quantity of short-wave photons, like the sun in summer. Late evening it switches into the Night Mode where it emits just long-wave light. Morning, the source switches back into the Day Mode.

It is favourable to connect the LED lamp into a block schemes in option DEN 1-4 (Colour or CCT switching bulb/LED luminaire):

All the four options have these common parts:
front-end circuit with overvoltage protection and a rectifier bridge, constant current source with isolation transformer, output power switches for the channels and control circuit with circuits to switch lighting modes.
 Option 1: switching between channels is performed directly by switching off and on in a certain sequence, the circuit selecting between lighting modes with own supply assesses switch-off of line supply itself. When the time for switch-off is exceeded the timing circuit for switch between lighting modes is reset.
 Option 2: switching between channels is performed directly by switching off and on in a certain sequence, the circuit selecting between lighting modes assesses switch-off of line supply independently. When the time for switch-off is exceeded the timing circuit for switch between lighting modes is reset.
 Option 3 for exterior luminaire: switching between channels is performed using a control circuit that uses external control signals for each channel. In this case, reset is not necessary under standard circumstances.
 Option 4 for exterior luminaire: switching between channels is performed using a programmed control system pre-programmed for certain light scenes or a radio-communication module transmitting control orders from a superior system. In this case, reset is not necessary under standard circumstances.

Figure 14:
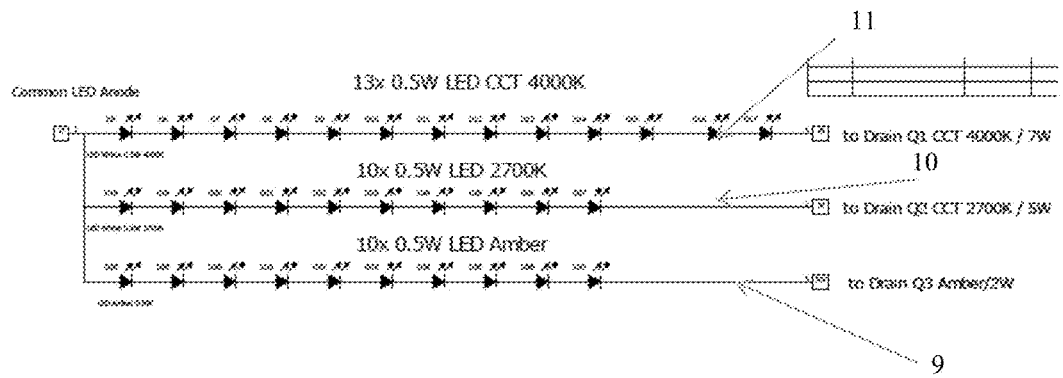
FIG. 14: Circuit diagram of LED lamp for DEN
Figure 15:
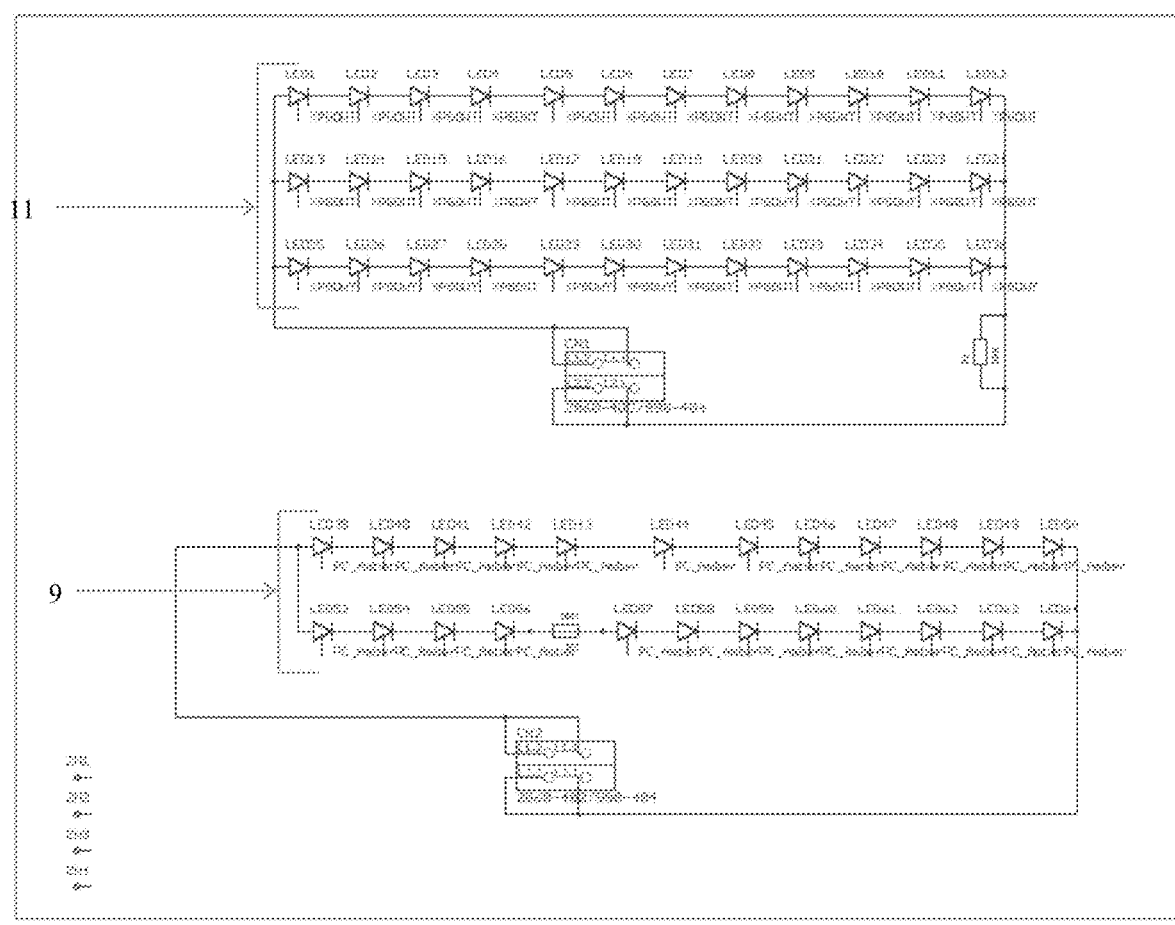
FIG. 15: Circuit diagram of I. and III. chain of outside lamp.
Figures 16, 17, 18:
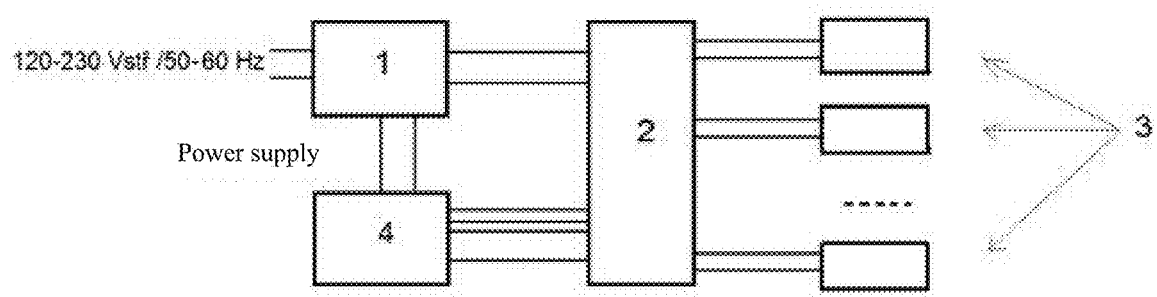
Figure 19:
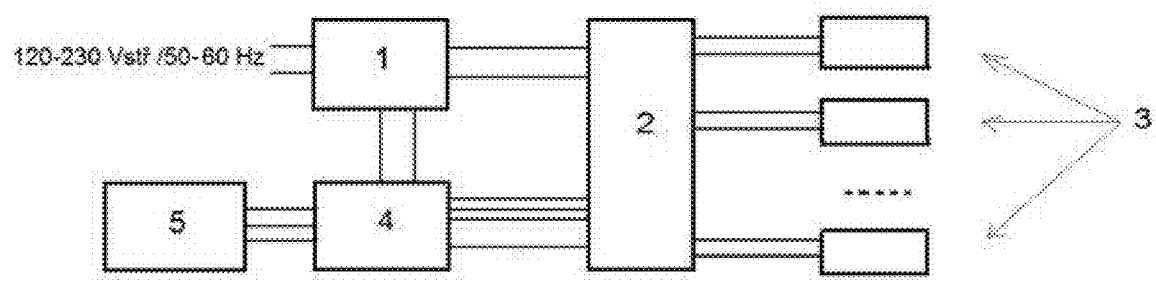
FIG. 19: Block scheme related to Example 8d.
Figure 20:
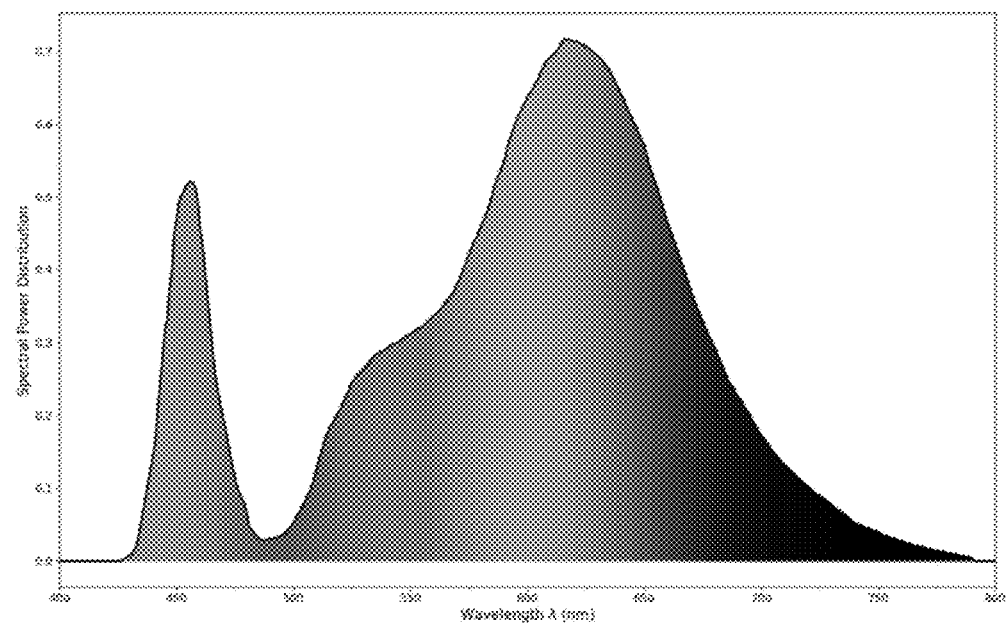
FIG. 20: Spectrum of luminophore with blue LED for 2700 K—II. chain, produced according to Example 2b.
Figure 23:
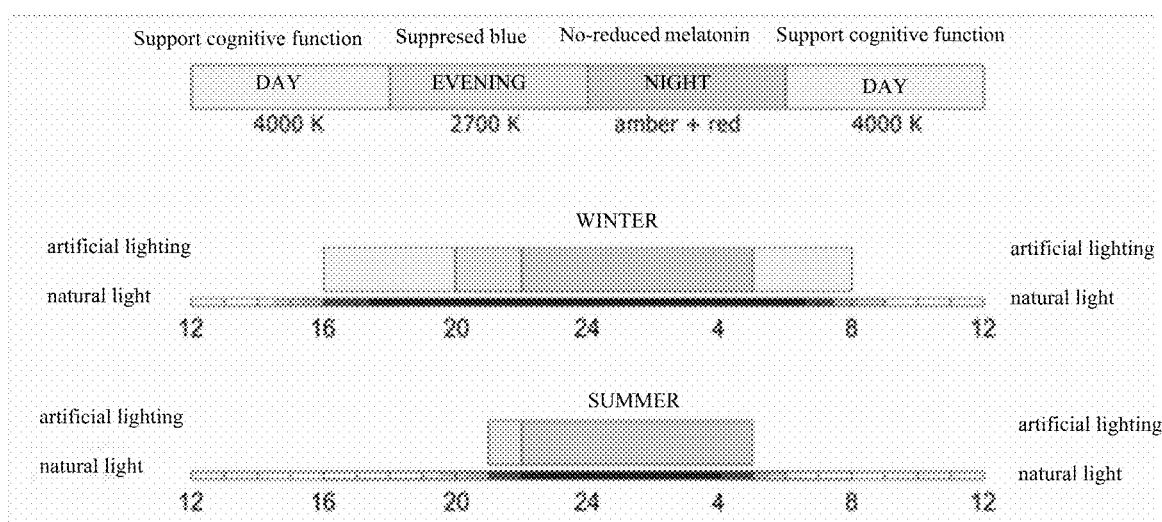
FIG. 23: Time schedule of lighting of public space using LED lamps
Figure 24:
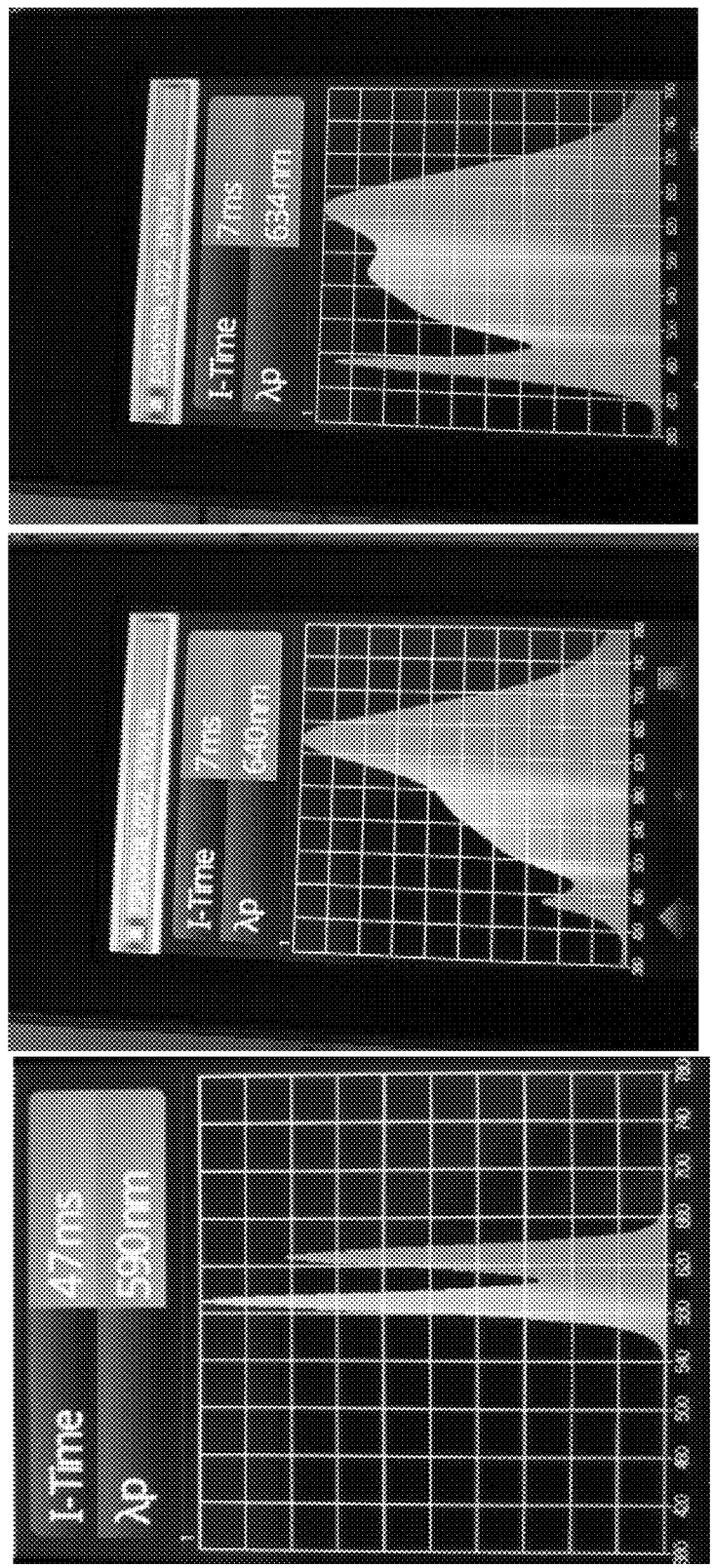
FIG. 24: Compilation of spectra of I. chain of LED lamp: amber:red 6:4, II. chain of LED lamp: CRI=98.3, blue 15%, green 25%, red 60% and III. chain of LED lamp: CRI=98, blue 25%, green 35%, red 40%
Figure 25:
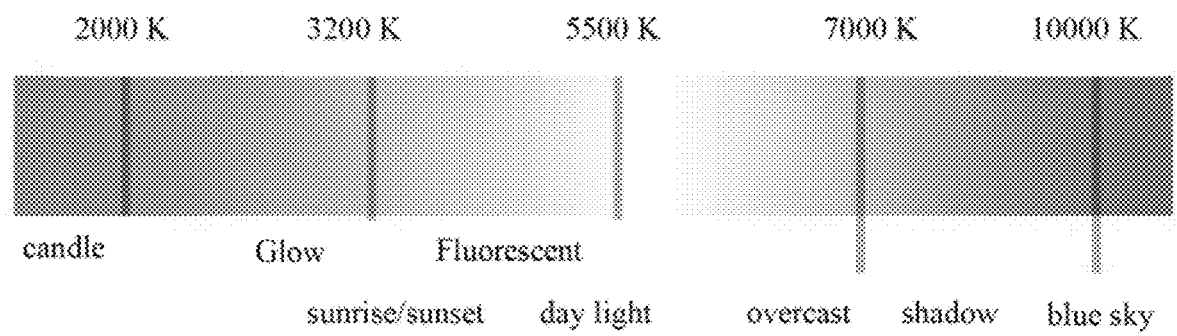
FIG. 25: Chromaticity temperature visualization
Figure 26:
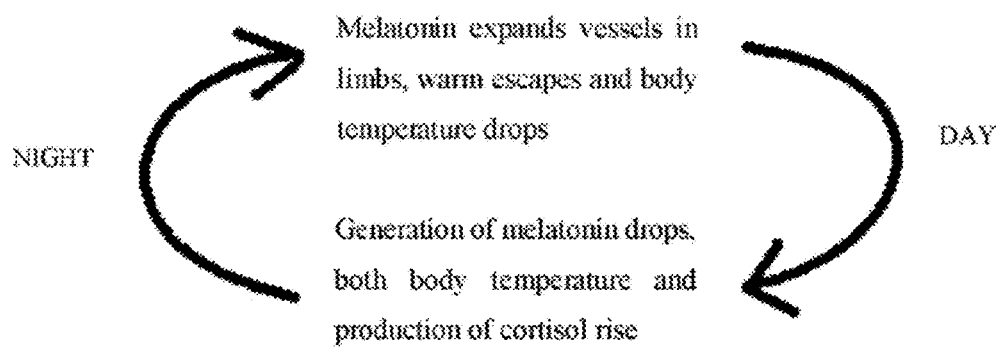
FIG. 26: Circle of melatonin during a day and night
Figure 27:
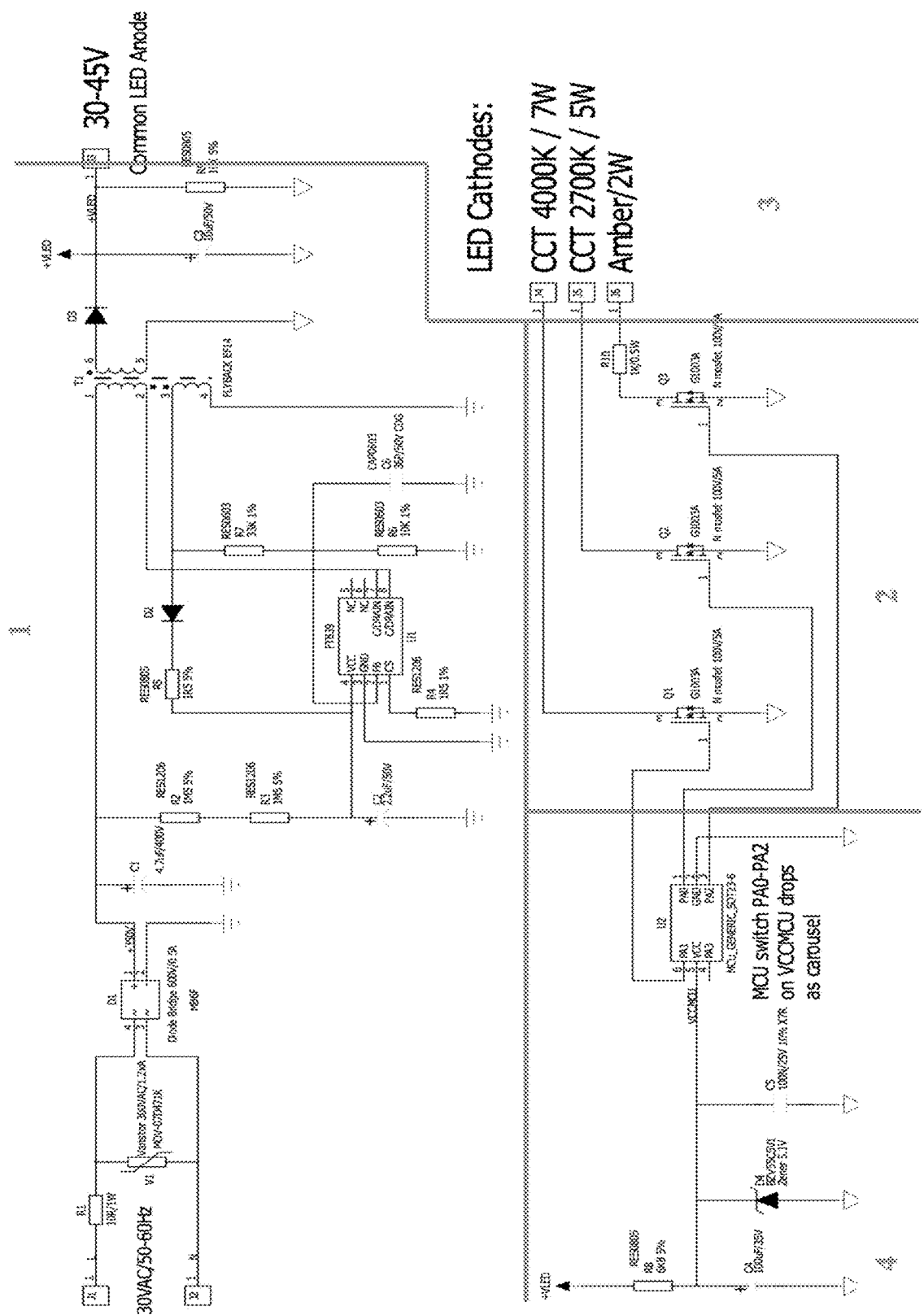
FIG. 27: Circuit diagram of LED lamp for DEN
Figure 28:
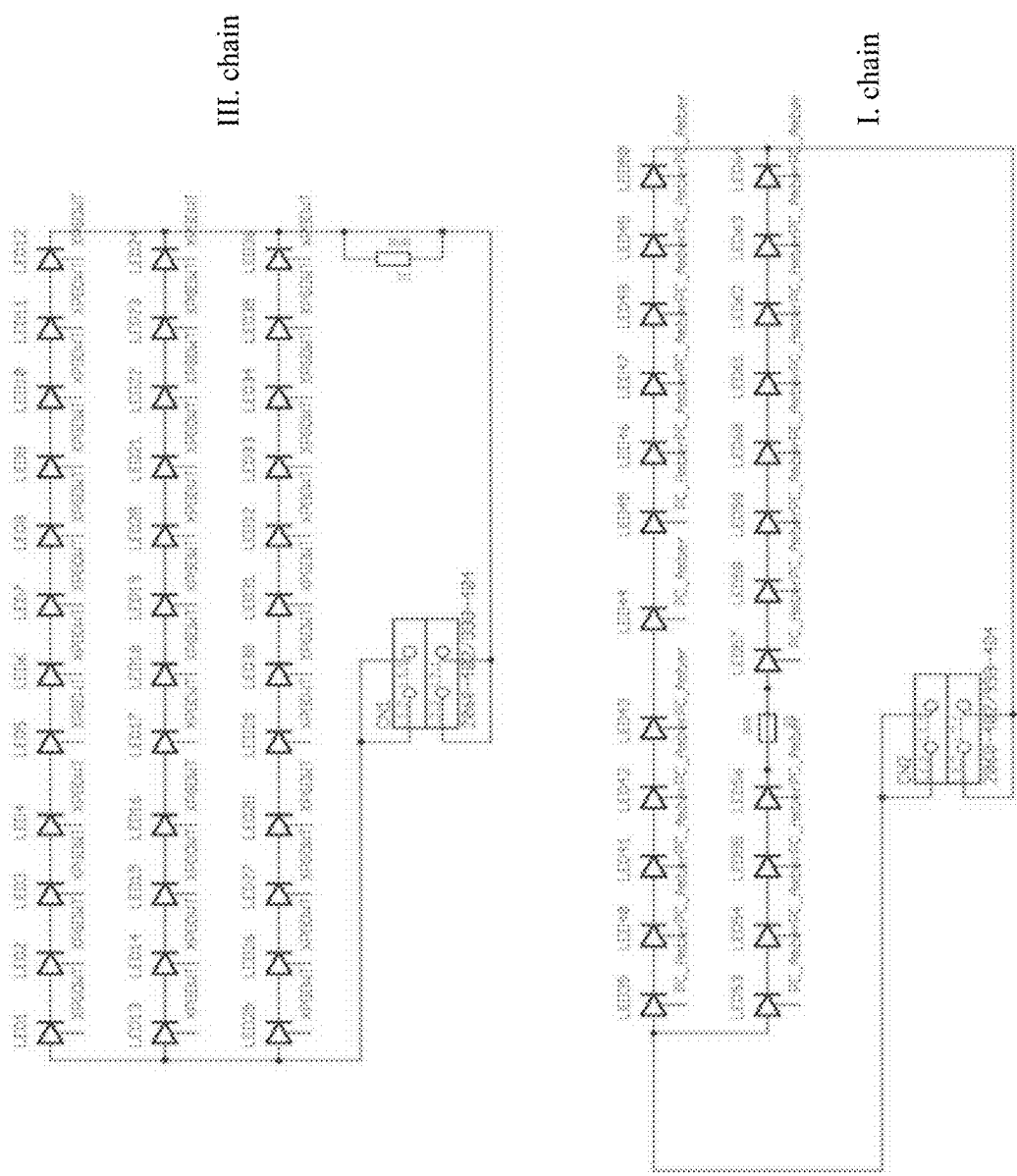
FIG. 28: Wiring diagram I. and III. Chains, strings according to Example 10
Figure 29:
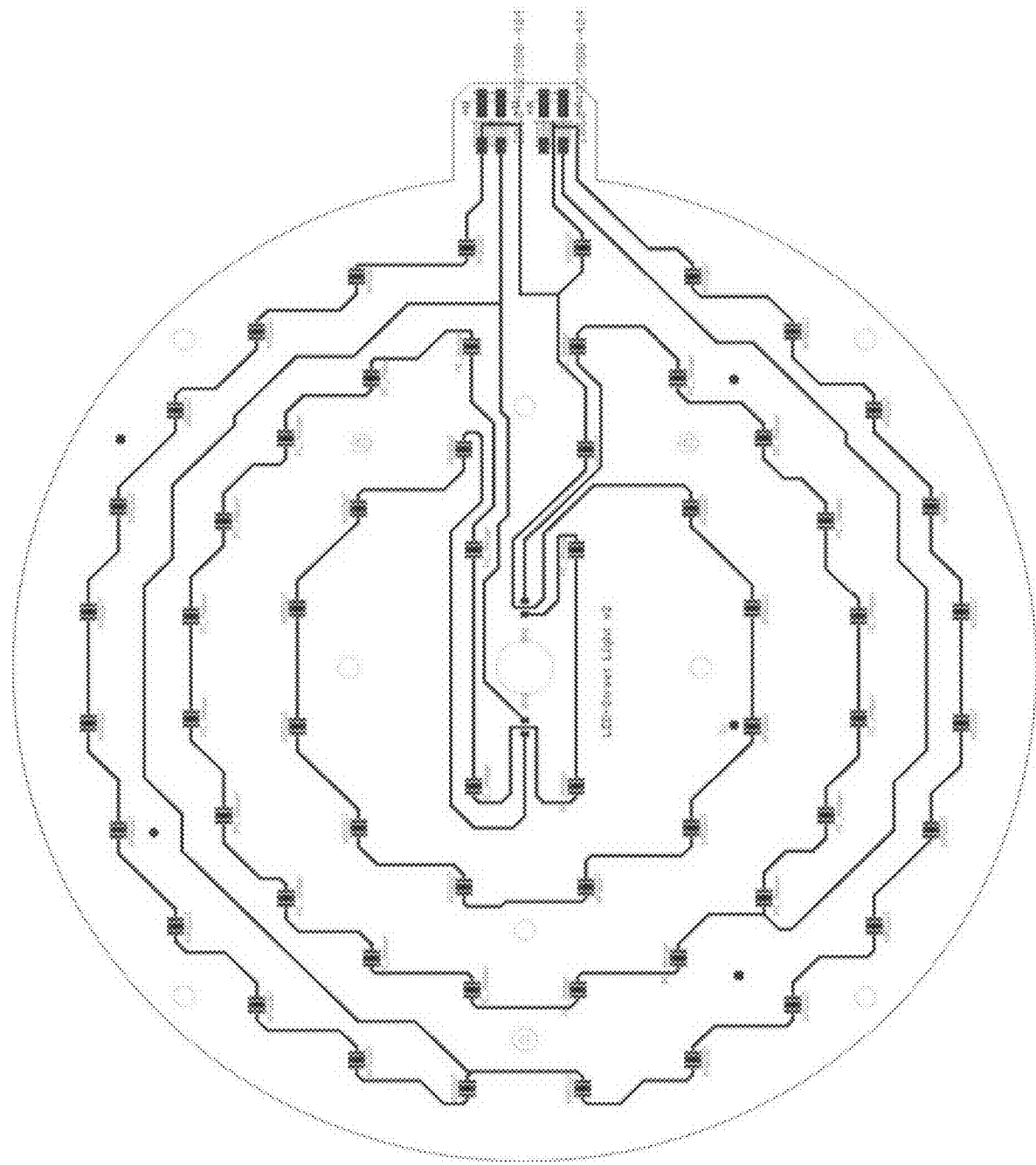
FIG. 29: Wiring diagram of the luminaire according to example 10
Figure 30:
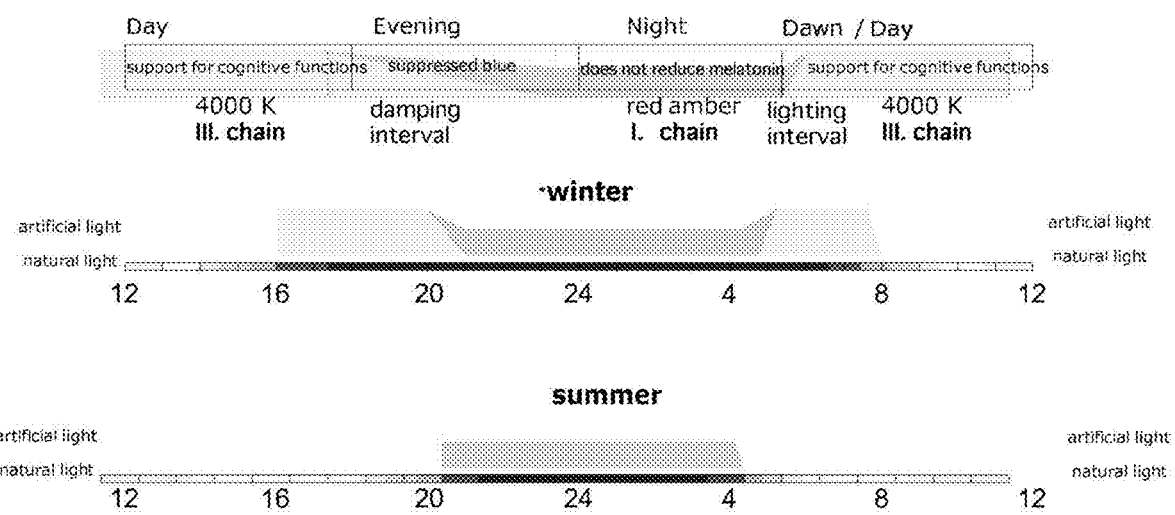
FIG. 30: Outdoor luminaire switching mode

Electric Circuit of LED Lamp (Application FIG. 14):

The electric circuit of a LED lamp consists of an input protection circuit consisting of R1 resistor providing for overcurrent protection, varistor V1 providing for overvoltage protection, further there are a rectifier bridge with filter C1 providing for supply of a current source consisting of circuit U1, supplied through resistors R2 and R3 with filter C2 and resistor R5 and diode D2 connected to winding of transformer T1 together with parallel combination of resistors R6 and R7, further resistor R4 and C6 providing for circuit timing, output winding of transformer T1 is connected through diode D3 to filtration capacitor C3 and resistor R9 which forms operating voltage +VLED for the sections of LED lamps, and then filtration capacitor C4 is supplied through resistor R8 and C5 providing for right time constant for "Option 1" with parallel Zener diode D4 setting operating voltage for control circuit U2 controlling shine of the relevant LED group, CCT/Amber using switch transistors Q1, Q2 and Q3 where resistor R10 limiting current in this circuit is connected to collector Q3.

An outside lamp is designed just of two chains. The III. chain switches on the light with chromaticity temperature 3800-4500 K first. It is advised to switch on this chain approximately from 4:30 p.m. to 8:00 p.m. in winter. Within this time range, people come from work, children from school and traffic is often heavy, and thus it is necessary to extend day light, particularly for safety. From 8.00 p.m. the traffic is not so heavy and people are home, ready to relax and prepare for bed. In this time the III. chain switches automatically into the I. chain which provides light with chromaticity temperature about 2500-2700 K. In summer when good visibility keeps even after 7.00p.m., it is advisable to switch on the III. chain automatically in public lighting e.g. from 8.00 p.m.

The source for outside lamp can be designed as follows: White chips with luminophore, red chips and amber chips can be inserted into a ceramic plate and it is favourable if ratio between amber and red chips is 4:5.

Automatic switch between the day and night modes which is favourable to use to outside lighting runs continuously namely in such a way that first the day mode is on, thus the III. chain—blur LED with luminophore. In the moment when the modes should turn, a circuit is switched using a switch to the I. chain and continuously current in the III. chain decreases while current in the I. chain, thus in red and amber chips, increases to 100% using a dimmer. The full transition from the day mode into the night mode shall occur when the current in the III. chain drops to 10% and the switch then disconnects it. The light does not change so that there is, for example, an unwanted frightening of a driver but the transition between chromaticity temperature 4000 K and 2672 K is gradual, slow and it will not affect anyone knowingly.

The maximum speed of switching the lighting modes, i.e. day-night, takes place over a period of 3 minutes, where every minute there is a 25% change in the value of the current supplied to the LED chips, in one chain from 100% to 0% and in the other chain from 0% to 100%.

The process of dimming, switching from daylight mode to nightlight mode: The exterior luminaire emits light in the Day mode, i.e. the chain III is energized, emitting white light, the supply current is supplied at 100%. The chain I is yet disconnected from the current. At the start of the switchover, the first reduction of the supply current to the chain III occurs at a maximum rate of 25% by reducing the value of the supply current in 1 minute either step-wise, a single step or a gradual decrease over the whole minute. At the same time, during this first minute, the value of the supply current to chain I increases, also at a maximum rate of 25% increase in the value of the current in 1 minute.

The entire process of switching between chains takes place at a maximum rate of 25% of the current value in 1 minute, both increasing and decreasing. These conditions are essential for an unobservable change during traffic on the roads and thus ensuring safety, where persons under such an exterior luminaire cannot be frightened.

Preferably, the switchover interval is set to 30 to 60 min, when the change in illumination is very gradual and completely imperceptible. Which is the ideal situation for a circadian-tuned luminaire.

Figure 31:
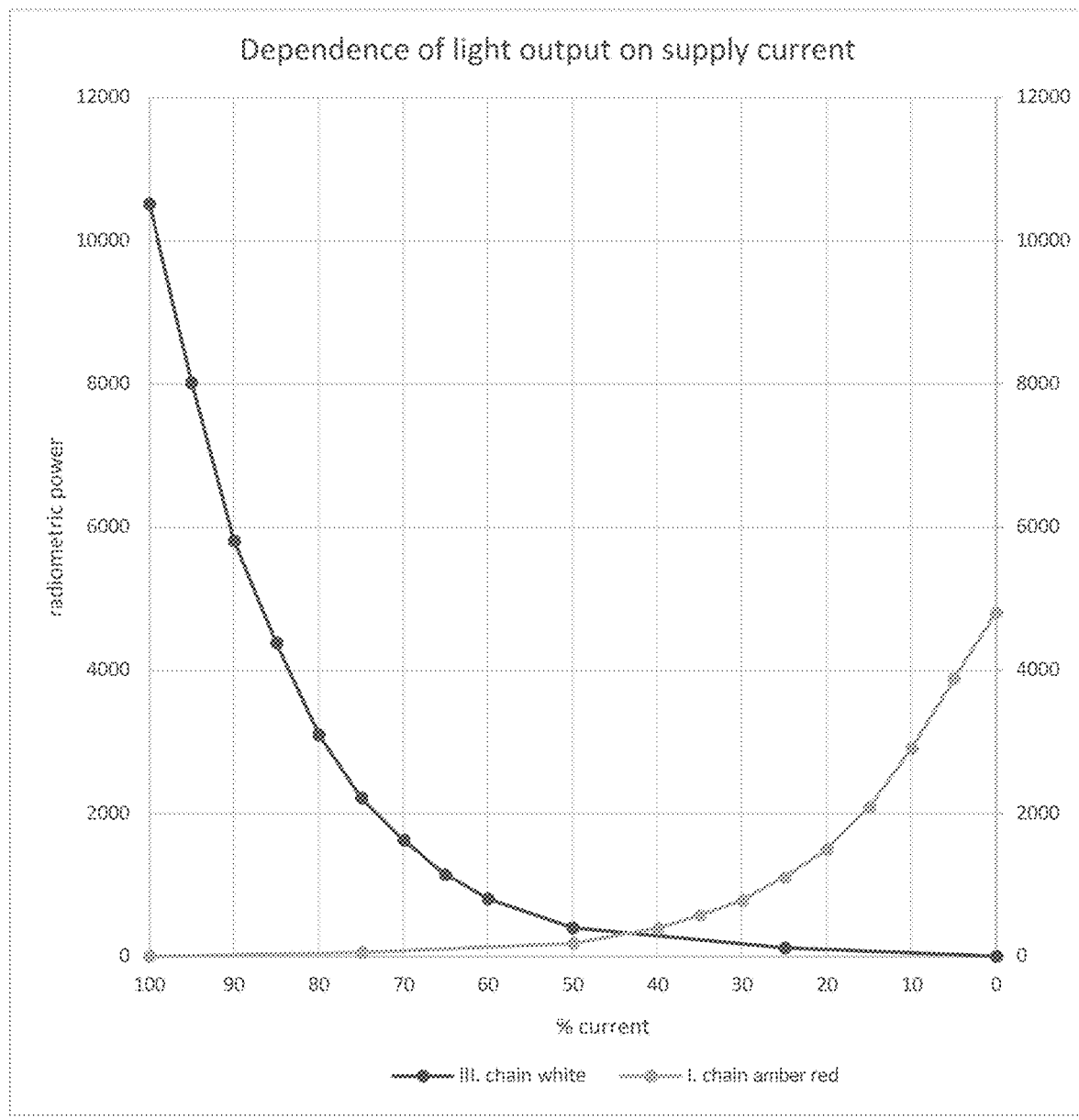
FIG. 31: Dependence of light output on supply current
Figure 32:
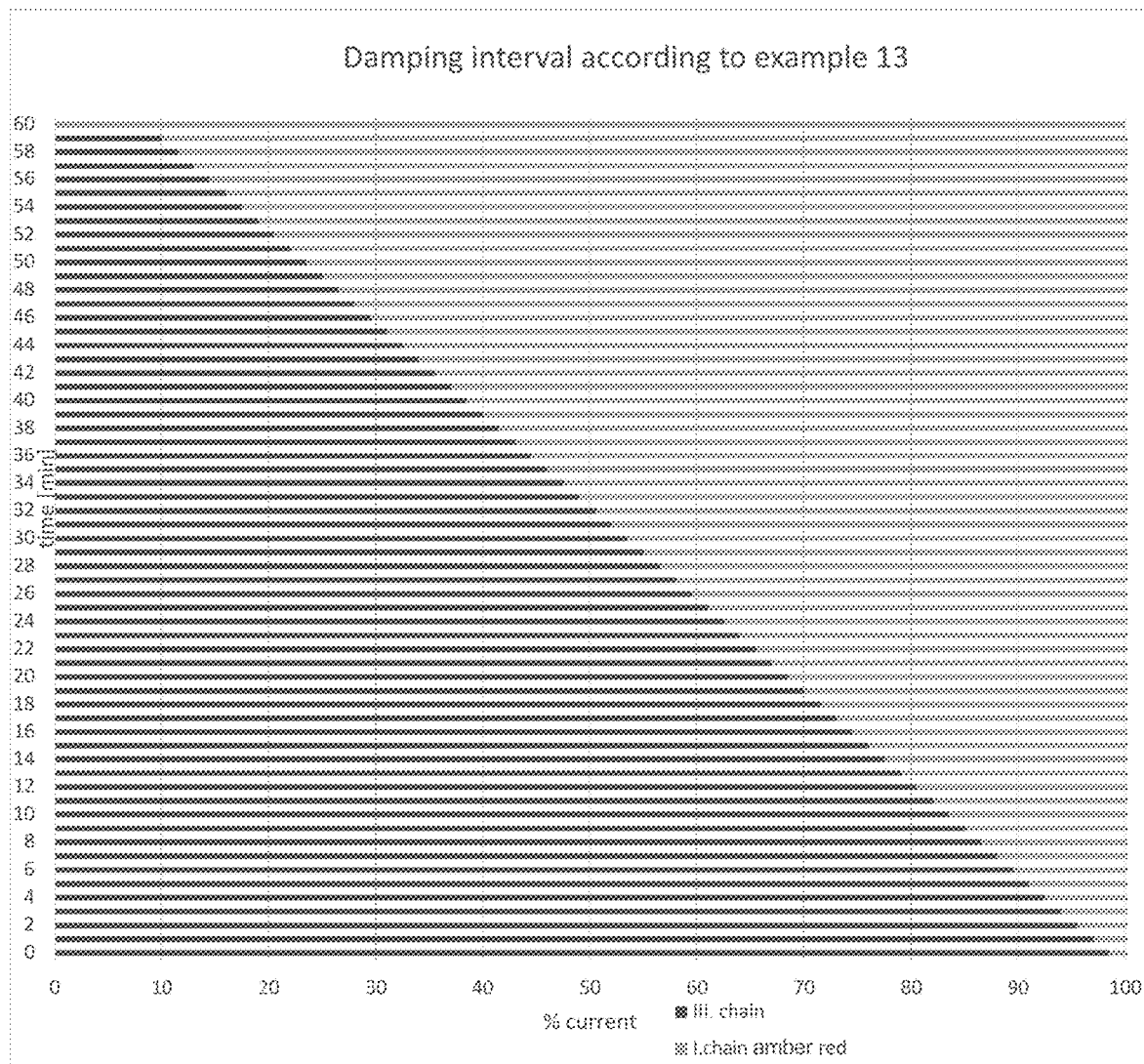
FIG. 32: Damping interval according to example 13
Figure 33:
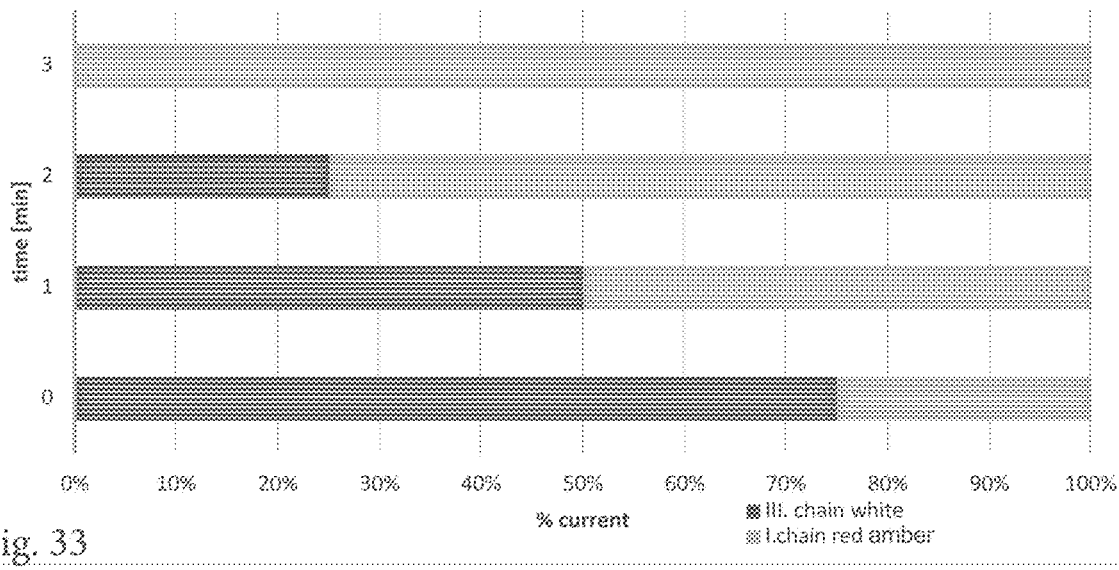
FIG. 33: Damping interval according to example 11
Figure 34:
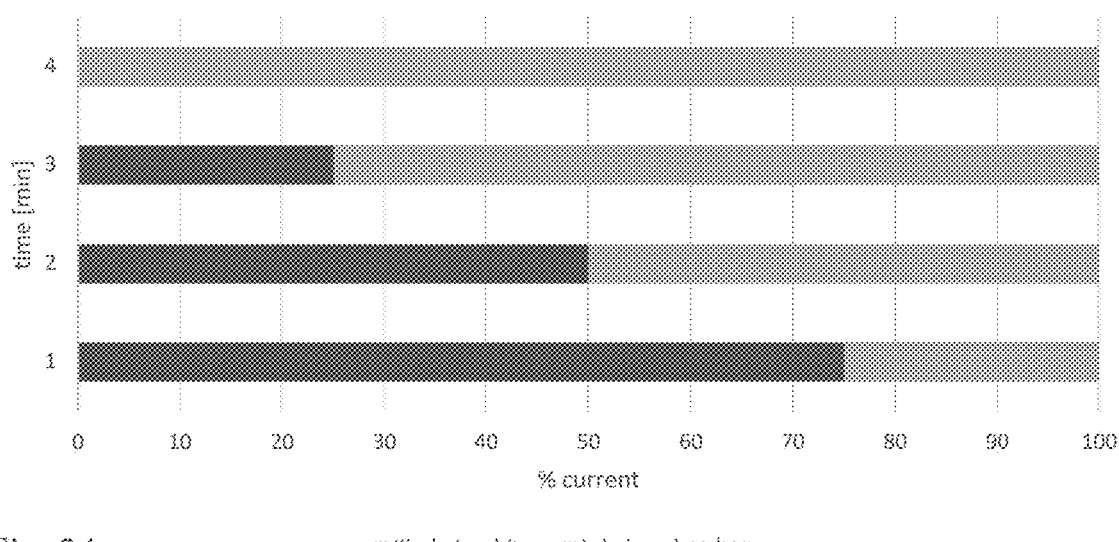
FIG. 34: Damping interval according to example 15
Figure 35:
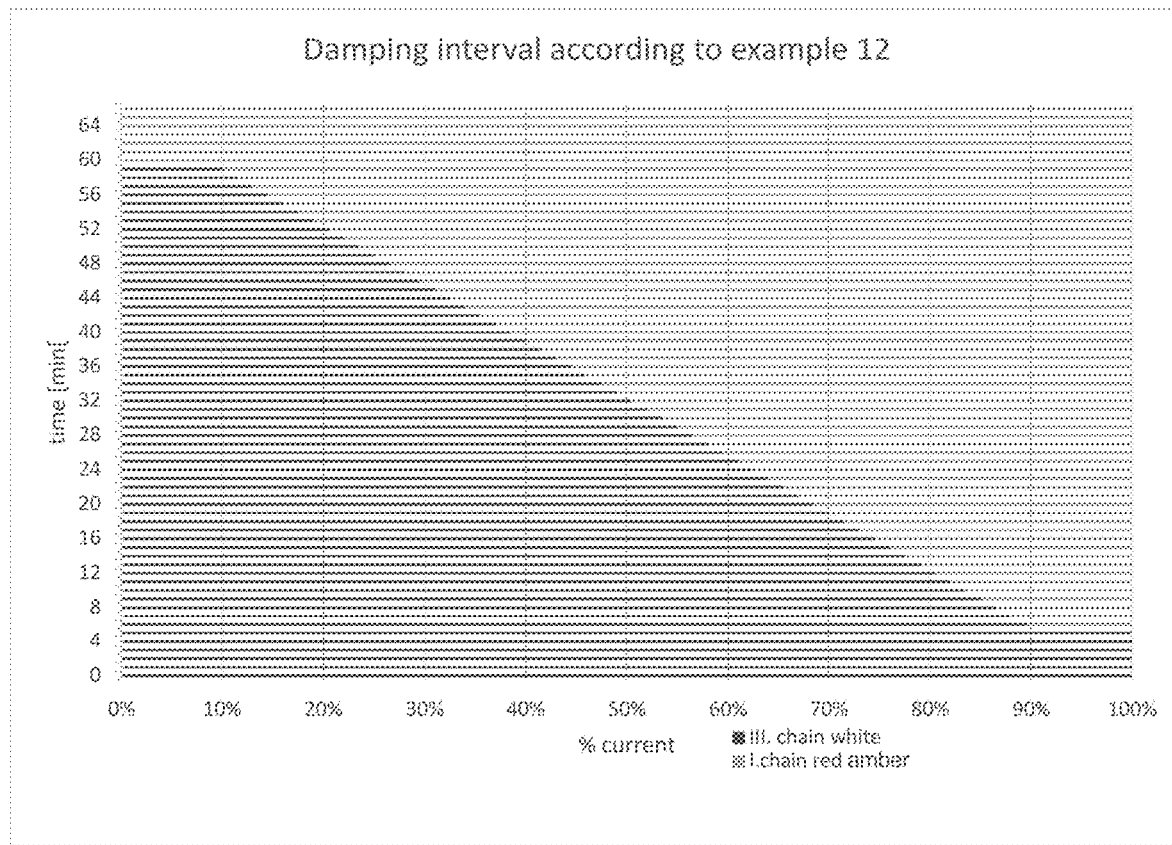
FIG. 35: Damping interval according to example 12
Figure 36:
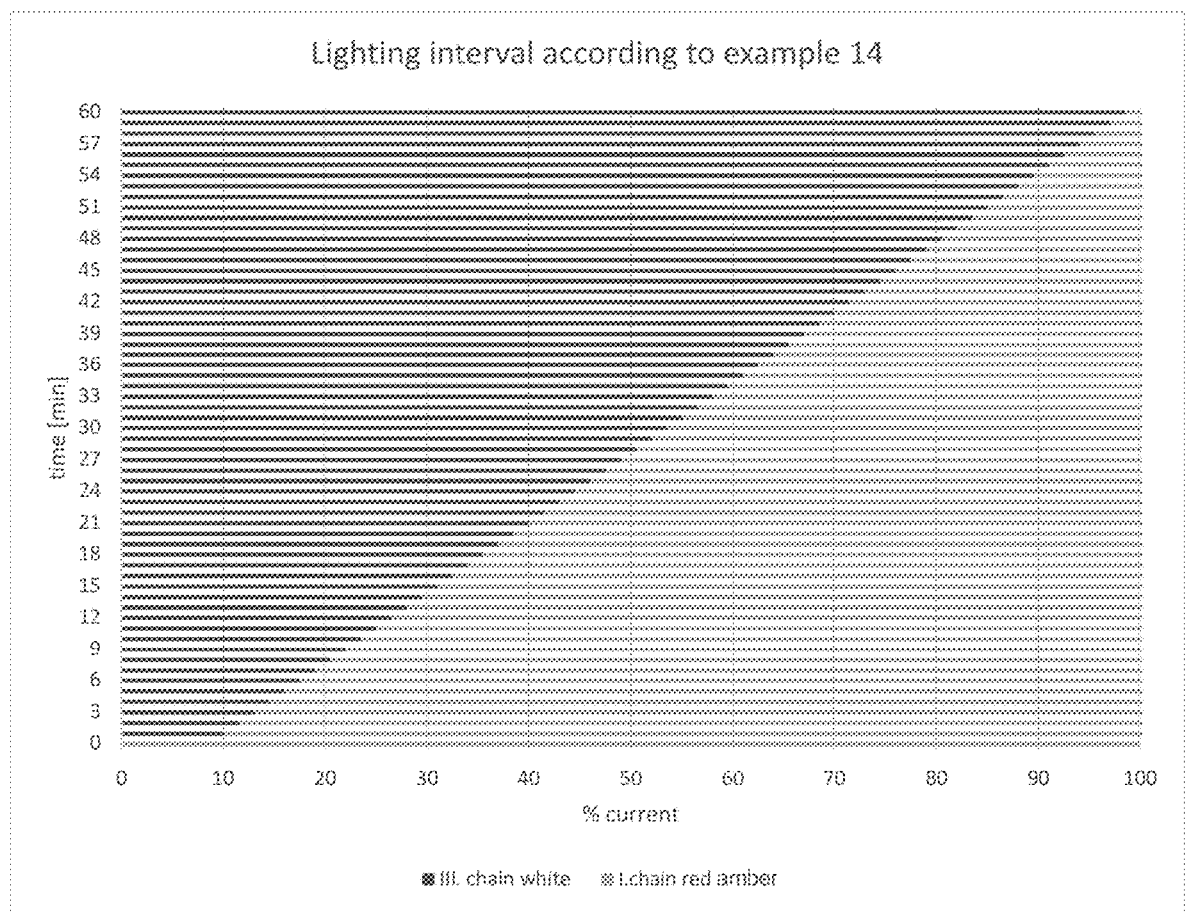
FIG. 36: Lighting interval according to example 14

The first and last 10% of value of the supply current is preferably fed or diverted in steps. Such a small influence of light is absolutely imperceptible, which is also clear from the dependence of radiometric power on % of supply current (see FIG. 31).

Gradual dimming of the light output on one chain while increasing the light output on the other chain is ensured by connecting each chain to a power source via a dimming ballast that regulates the power supply currents on each chain separately.

The 100% value of the supply current on chain III corresponds to approximately half the luminance value of the 100% value of the supply current on chain I. That means that the chain I, at the maximum power setting, achieves about half of the maximum light output setting of the chain III. Thus, at night the exterior luminaire emits with half the luminous intensity than during the day and at the same time completely without the blue component, which disrupts the circadian rhythm of the organism.

The switchover mode is preferably controlled based on an external signal either from the astrodyme or via a digital or analogue protocol to the dimming ballast or remotely manually.

EXAMPLES

Example 1: Production of LED Lamp for Evening Mode—2700 K a) Semiconductor InGaN and Luminophore NaLuS2

First the luminophore was produced, it originated from $Na_2CO_3$ and $LuO_3$ in a chemical reaction in $H_2S$ atmosphere. A mixture of oxides was placed in an alumina tray into an alumina tube and the mixture was slowly heated in an electric resistance furnace to temperature 1200° C. under argon atmosphere. Then the mixture was annealed in $H_2S$ atmosphere for 80 minutes and then slowly cooled approximately by 1° C. per minute. After room temperature was achieved, the resulting product was decanted in water and then in alcohol and then stored in argon atmosphere. The formed crystals were small plates 0.3 mm thin. The small plates were glued to a blue chip with InGaN composition. Finally, the chip covered with luminophore was coated with silicone binding agent.

b) Semiconductor ZnSe and Mixture of Luminophores ZYP555G3 and ZYP63063 in Ratio 3:4

Commercial powder luminophores labelled ZYP555G3 emitting light spectrum with maximum at 628 nm and ZYP63063 emitting maximum at 555 nm were mixed in ratio 3:4. 0.5 g of powder mixture dispersed in silicone was applied on a blue LED with semiconductor ZnSe, silicone served as powder carrier. A wall of the LED bed was inclined by 20° against the level in which the light goes out.

This way a light source with colour spectrum in ratio blue (455 nm):green (555 nm):red (628 nm) 0.55:0.58:1.10 was produced. The resulting radiated light from the LED had chromaticity temperature of 2700 K.

Example 2: Production of Light Source for Night Mode DEN—4000 K a) Semiconductor InGaN and Luminophore YAG:Ce First, luminophore was prepared that consisted of powder oxides: $Y_2O_3$, $\alpha$-$Al_2O_3$ and $CeO_2$ which were weighted and mixed in stoichiometric ratio (Y+Ce):Al=3:5. Ce concentration was 0.1 at. %. The mixture of oxides was ground in a ball grinder for 8 hours and then dried and sieved. Then the mixture of oxides was calcited in air at 600° C. for 4 hours. Calcited powder was created, it was compacted to form a ceramic body with diameter 18 mm using uniaxial press with force 5 MPa and cold isostatic press with force 250 MPa. The body was sintered at 1700° C. for 20 hours in vacuum atmosphere. The generated luminophore had composition $Y_3Al_5O_{12}$:Ce and thickness 0.2 mm. This way prepared luminophore was glued to a blue LED chip of InGaN composition. Finally, the chip with luminophore was coated with silicone binding agent.

This way a light source with colour spectrum in ratio blue (455 nm):green (555 nm):red (628 nm) 0.5:1.0:0.65 was produced. The resulting radiated light from the LED had chromaticity temperature of 3098 K.

b) Semiconductor SiC and Mixture of Luminophores ZYP555G3 and ZYP63063 in Ratio 1:2

Commercial powder luminophores labelled ZYP555G3 emitting maximum at 555 nm and ZYP63063 emitting maximum at 628 nm were mixed in ratio 1:2. 0.4 g of powder mixture dispersed in silicone was applied on a blue LED with semiconductor SiC, silicone served as powder carrier. A wall of the LED bed was inclined by 20° against the level in which the light goes out.

This way a light source with colour spectrum in ratio blue (455 nm):green (555 nm):red (628 nm) 0.8:1.0:0.75 was produced. The resulting radiated light from the LED had chromaticity temperature of 4000 K.

Example 3: Production of LED Lamp of DEN Type 33 chips in three rings were positioned on a ceramic plate. 13 blue chips with composition of InGaN semiconductor coated with luminophore according to Example 2a) were positioned in the outer ring. 10 blue chips with composition of InGaN semiconductor coated with luminophore according to Example 1a) and 4 red chips with composition of AlGaInP semiconductor were inserted in the middle ring. 6 amber chips with composition of GaAsP semiconductor were positioned in the inner ring.

33 chips in three rings were positioned on a ceramic plate. 13 blue chips with composition of SiC semiconductor coated with luminophore according to Example 1b) were positioned in the outer ring. 10 blue chips with composition of ZnSe semiconductor coated with luminophore according to Example 2b) and 4 red chips with composition of GaP semiconductor were inserted in the middle ring. 6 amber chips with composition of AlGaInP semiconductor were positioned in the inner ring.

Example 4: Using Light Source of DEN Type a) A LED lamp manufactured according to Example 3a) can be switched into three chains using any switch. A switch on the lamp or a switch on a wall can be used.

After the switch is on, the light of the I. chain is on and the only active chips were amber and red ones and radiated monochromatic light had wavelength of 580 nm. Switchover had activated the II. chain and the only active chips were those positioned in the middle ring with luminophore according to Example 1a), and blue light was emitted and a part of light was transformed by luminophore to yellow light. Mixing of these colours created warm white light with wavelengths in range 380-750 nm. After repeated switchover, the III. chain was activated and the only active chips were those positioned in the outer ring with luminophore according to Example 2a), and blue light was emitted and a part of light was transformed by luminophore to yellow light. Mixing of these colours created warm white light with wavelengths in range 380-680 nm.

Switching-off and repeated switching-on after a period exceeding 10 s caused always activation of lights of the I. chain only with monochromatic amber and red LEDs.

I. chain—2 W, 592 nm
Having been switched, the bulb will light with monochromatic amber and red, suitable for night vision which does not disturb the circadian rhythms.

II. chain—5 W, 2700 K, 97 Ra, 330 lm
The second stroke switches on warm white colour simulating light 45 minutes before sunset.

III. chain—7 W, 4000 K, 97 Ra, 490 lm
The third stroke switches on day white colour that has the same parameters as mid-day sun. The day mode is suitable for work, it keeps a man alert.

b) A LED lamp manufactured according to Example 3b) can be switched into three chains using any switch. A switch on the lamp or a switch on a wall can be used.

After the switch is on, the light of the I. chain is on, and the only active chips were red and amber ones and radiated monochromatic light had wavelength of 595 nm. Switchover had activated II. chain, the only active chips were those positioned in the middle ring with luminophore according to Example 1b), and blue light was emitted and a part of light was transformed by luminophore to yellow light. Mixing of these colours created warm white light with wavelengths in range 380-750 nm. After repeated switchover, the III. chain was activated and the only active chips were those positioned in the outer ring with luminophore according to Example 2b), and blue light was emitted and a part of light was transformed by luminophore to yellow light. Mixing of these colours created warm white light with wavelengths in range 380-680 nm.

Switching-off and repeated switching-on after period exceeding 10 s caused always activation of lights of the I. chain only with monochromatic red and amber LEDs.

I. chain—LED chip 2 W, 592 nm
Having been switched, the bulb will light with monochromatic amber, suitable for night vision, which does not disturb the circadian rhythms.

II. chain—LED chip 5 W, 2700 K, 97 Ra, 330 lm
The second stroke switches on warm white colour simulating light 90 minutes before sunset III. chain—LED chip 7 W, 4000 K, 97 Ra, 490 lm
The third stroke switches on day white colour that has the same parameters as mid-day sun. The day mode is suitable for work, it keeps a man alert.

Example 5: Production of Light Source for Outside Lighting

Blue LED with Luminophore+Amber+Red LED

Blue chips with luminophores were prepared according to Example 1a). Amber chips consisted of semiconductor with GaAsPN composition with ratio of elements Ga:As:P:N=1: 0.15:0.85:1. Red chips consisted of semiconductor with GaAsP composition with ratio of elements Ga:As:P=1:0.6: 0.4.

Example 6: Production of LED Lamp for Outside Lighting

According to Example 5, 56 chips in four rings were positioned on a ceramic plate. 24 blue chips covered with luminophore were positioned in the outer ring. 12 amber chips and 8 red chips were inserted in the next ring. 12 blue chips covered with luminophore were positioned in the next ring and 4 amber chips were positioned in the central ring.

Example 7: Using Light Source for Outside Lamp

Blue LED s Luminophore+Amber+Red LED
A LED lamp manufactured according to Example 6 can be switched into two modes automatically.

After switch, the first mode is activated and all the chips positioned on the ceramic plate were active. Blue light from the LED was emitted and a part of light was transformed by luminophore to yellow light. Mixing of these colours produced white light with wavelengths in range 380-680 nm and chromaticity temperature of 3855 K and CRI=82.4. Continuous regulation activated the II. chain where only red and amber chips were on with chromaticity temperature of 2672 K.

The LED lamp is switched automatically or manually into three or two modes with CCT and spectral composition suitable for the corresponding part of the day:

Mode Night, amber light not disturbing production of hormone melatonin, with markedly suppressed share of short-wave photons or completely without the short-wave component (provides for good sleep).

Mode Evening, warm yellow light similar to classic glow-bulb or sun before sunset, with small share of short-wave/blue photons (suitable for relaxation).

Mode Day, white day light similar to sun during a day, with marked share of short-wave photons (supports cognitive performance of brain).

In case of manually switched inside LED lamp with three lighting modes, the switch over is carried out through repeated stroke on the switch in interval less than 10 s. Automatically switched LED lighting is suitable for public lighting.

Example 8: Description of the Block Schemes a) The control system switches colour and/or chromaticity temperature CCT through detection of current loss.
First switch ON: I. chain. Switch OFF and switch ON again: II. chain Switch OFF and switch ON again: III. chain
A big capacitor is used to keep the system in the previous state.

b) The control system switches colour and/or chromaticity temperature CCT through detection of current loss.
First switch ON: I. chain
Switch OFF and switch ON again: II. chain Switch OFF and switch ON again: III. chain
A big capacitor is used to keep the control circuit in the previous state. This practice can achieve shorter time in OFF state notwithstanding a change stored in the capacitor in an AC/DC converter.

c) The control system switches colour and/or chromaticity temperature CCT using a control wire.
The control wire switches colour LED and/or chromaticity temperature CCT directly without sequencing. The control circuit carries out filtering and transmits voltage from the control wire to a LED chain.

d) The control system switches colour and/or chromaticity temperature CCT through request to PLC (Power-line) and/or a wireless communication module.
PLC and/or a wireless communication module switches directly between a LED colour and/or chromaticity temperature CCT without sequencing.

Example 9: Electric Circuit of LED Lamp a) Using NMOSFET

The source of supply voltage is connected through connection of the protective resistor (R1) for overcurrent protection and the varistor (V1) for overvoltage protection to input of the block (1) of the constant current source with the isolation transformer consisting of the rectifying circuit (D1), and its positive voltage output is connected with the positive electrode to the first filtration capacitor (C1) with the earthed negative electrode, and with the serial combination consisting of the resistors (R2, R3) and the second filtration capacitor (C2) earthed on its other end with its negative electrode where the common point of the third resistor (R3) and the positive electrode of the second capacitor (C2) of this serial combination is connected to input of supply to the current source (U1) where the third input of the isolation transformer winding (T1) together with the earthed serial combination of the sixth and seventh resistors (R6, R7) is connected through the fifth resistor (R5) and the second diode (D2) in direction cathode-anode, and where the fourth input of the isolation transformer (T1) is earthed, and the earthed fourth resistor (R4) and the sixth capacitor (C6) providing for timing are connected to the timing inputs of the current source circuit (U1), and the output of the rectifying circuit (D1) is connected to the first input of the isolation transformer (T1), and its output winding is through its output (6) connected through the third diode (D3) in forward direction to the positive electrode of the filtration third capacitor (C3) and to the ninth resistor (R9) to generate output voltage (+V LED) for the sections of LEDs, where this voltage (+V LED) is connected to anode input of the LED chains (3), and then the output voltage (+V LED) is connected into the block (4) of the control circuit of the channel switches, namely to the serial combination of the eighth resistor (R8) with the parallel combination of the filter fourth and fifth capacitors (C4, C5) to determine the required time constant, where to this parallel combination of the fourth and fifth capacitors (C4, C5) the Zener diode (D4) is connected to determine operating voltage of the second control circuit (U2) implementing the block (4) of the control circuit of the channel switches to control the LED chains (3) to change the lighting mode where outputs from the control circuit (U2) are connected to the LED chains (3) using NMOSFET switch elements, namely they are connected to electrodes (G) of the switch elements (Q1 to Q3), and their terminals (D) are connected to the cathode output of the LED chain (3) of type CCT 4000K/7 W, to the cathode output of the LED chain (3) of type CCT 2700K/5 W and through the current-limiting tenth resistor (R10) to the cathode output of the LED chain (3) of the amber type/2 W, b) Using NPN Transistors The source of supply voltage is connected through connection of the protective resistor (R1) for overcurrent protection and the varistor (V1) for overvoltage protection to input of the block (1) of the constant current source with the isolation transformer consisting of the rectifying circuit (D1), and its positive voltage output is connected with the positive electrode to the first filtration capacitor (C1) with the earthed negative electrode, and with the serial combination consisting of the resistors (R2, R3) and the second filtration capacitor (C2) earthed on its other end with its negative electrode where the common point of the third resistor (R3) and the positive electrode of the second capacitor (C2) of this serial combination is connected to input of supply to the current source (U1) where the third input of the isolation transformer winding (T1) is connected through the fifth resistor (R5) and the second diode (D2) in direction cathode-anode together with the earthed serial combination of the sixth and seventh resistors (R6, R7) where the fourth input of the isolation transformer (T1) is earthed, and the earthed fourth resistor (R4) and the sixth capacitor (C6) providing for timing are connected to the timing inputs of the current source circuit (U1), and the output of the rectifying circuit (D1) is connected to the first input of the isolation transformer (T1), and its output winding is through its output (6) connected through the third diode (D3) in forward direction to the positive electrode of the filtration third capacitor (C3) and to the ninth resistor (R9) to generate output voltage (+V LED) for the sections of LEDs, where this voltage (+V LED) is connected to anode input of the LED chains (3), and then the output voltage (+V LED) is connected into the block (4) of the control circuit of the channel switches, namely to the serial combination of the eighth resistor (R8) with the parallel combination of the filter fourth and fifth capacitors (C4, C5) to determine the required time constant, where to this parallel combination of the fourth and fifth capacitors (C4, C5) the Zener diode (D4) is connected to determine operating voltage of the second control circuit (U2) implementing the block (4) of the control circuit of the channel switches to control the LED chains (3) to change the lighting mode where outputs from the control circuit (U2) are connected to the LED chains (3) using switch elements of bipolar NPN transistors, namely they are connected to bases of the switch elements (Q1 to Q3), and their collectors are connected to the cathode output of the LED chain (3) of type CCT 4000K/7 W, to the cathode output of the LED chain (3) of type CCT 2700K/5 W and through the current-limiting tenth resistor (R10) to the cathode output of the LED chain (3) of the amber type/2 W.

Example 10: Exterior Luminaire Assembly

The circular printed circuit was fitted with LED chips in two chains, chain III with 36 white LED chips, i.e. blue LED chips overlaid with a luminophore with a correlated color temperature CCT of 4000 to 2200 K, with an output of about 1.5 W and a total output of chain III of 55 W, with an illuminating power of 117 lm/W. Chain I with 16 monochromatic amber LED chips emitting orange light from the wavelength range 580 nm to 610 nm with a single chip power of 2 W and a single chip radiometric power of 20 mW, 8 red LED chips emitting red light from the wavelength range 610 nm to 700 nm with a single chip power of 2 W and a single chip radiometric power of 35 mW. The chips were placed in series-parallel with 12 chips in a series. The chains were connected to a power supply via a dimming ballast (ballast resistor) with a voltage window of 20 to 50 V and power up to 70 W. The total voltage supplied was 36 V, i.e. to the LED chips in five parallel branches of 3 V per chip. The dimming ballast was connected via DALI protocol to the remote control using control voltage, where the current in chain III was gradually reduced from 100% of the original value to 0%, for this arrangement from 900 mA to 0 mA. And the current in chain I was gradually increased from 0% to 100%. This resulted in a gradual to smooth transition from evening light to night light. Thus, from the illumination of chain III containing the blue light component to the illumination of chain I completely without the blue light component.

Example 11: Step Model of Dimming from Evening to Night of Exterior Luminaire Under Example The dimmer was controlled by a digital protocol to switch from daylight mode via chain III to nighttime mode via chain I. The switchover interval was set to 3 minutes. When the switching mode control is initiated, the input supply current to chain III is reduced by 25% and the supply current to chain I is switched on to 25% of its set point. After one minute, the supply current to chain III was further reduced to 50% of the total and the supply current to chain I was further increased to 50% of the total. After the second minute, the supply current to chain III was further reduced to 25% of the total and the supply current to chain I was further increased to 75% of the total. After the third minute, the supply current to chain III is switched off and the supply current to chain I is further increased to 100% of the total. This process gradually switched the lighting modes from evening to night.

Example 12: Gradual Model of Dimming from Evening to Night of Exterior Luminaire The dimmer was controlled by the digital protocol in the early evening, when it was already dark, to switch from daytime lighting via chain III to nighttime lighting via chain I. The switchover interval was set to 66 minutes. After the start of the switching mode control, the supply current to chain III was reduced continuously or in small steps by the dimming ballast and at the same time the supply current to chain I was increased in the same way. The step change in current was set to 1.5% in 1 minute. Thus, at the start of the switching mode, there was a first reduction of 1.5% of the current value on chain III, in the next minute there was a further reduction of another 1.5% of the current value, this continued until minute 6 when the current value dropped by 10.5% and as the current on chain III dropped, the current on chain I increased by 10.5%. In the 7th minute there was already a decrease in current on chain III by another 1.5% and an increase in current on chain I by 1.5%.

The first 10% is a completely insignificant light source to the human eye and therefore does not need to be stepped and the control protocol is simplified. The dimming process of chain III was completed after 60 min and the lighting process of chain I was completed after 66 min as it was started after 6 min from the start of the switchover interval.

Example 13 Gradual Model of Dimming from Evening to Night of Exterior Luminaire

The dimmer was controlled by the digital protocol in the evening, when it was already dark, to switch from daytime lighting via chain III to nighttime lighting via chain I. The switchover interval was set to 60 minutes. After the start of the switching mode control, the supply current to chain III was reduced continuously in small steps by the dimming ballast and at the same time the supply current to chain I was increased in the same way. The change in current was set to 1.5% in 1 minute. Thus, at the start of the switching mode, there was a first reduction of 1.5% of the current value on chain III, in the next minute there was a further reduction of another 1.5% of the current value, this continued until minute 59 when the current value dropped by 10% and in minute 60 the input current to chain III was disconnected completely. As the current on chain III dropped, the current on chain I increased. In the first minute the input current to chain I was set to 10.5%. In the second minute, the current increment on chain I was already set to the standard 1.5% until minute 60, when the light source was already illuminating only through chain I.

The first 10% is a completely insignificant light source to the human eye and therefore does not need to be graduated and the control protocol is simplified. The dimming process of chain III was completed at minute 60, when chain III was completely de-energized and the illumination process of chain I was completed. The light source was on all night in this night mode through chain I, and before dawn the process was repeated in reverse order. The current fed to chain I decreased and the current fed to chain III increased. After dawn, the light source was completely disconnected from the power supply until dusk, when the illumination process began.

Example 14: Gradual Model of Illumination from Night to Day of Exterior Luminaire The dimmer was controlled by a digital protocol before dawn, when the morning rush hour is already out there and it is still dark, to switch from nighttime lighting via chain I to daytime lighting via chain I. The switchover interval was set to 60 minutes. After the start of the switching mode control, the supply current to chain I was reduced continuously in small steps by the dimming ballast and at the same time the supply current to chain III was increased in the same way. The change in current was set to 1.5% in 1 minute. Thus, at the start of the switching mode, there was a first reduction of 1.5% of the current value on chain I, in the next minute there was a further reduction of another 1.5% of the current value, this continued until minute 59 when the current value dropped by 10% and in minute 60 the input current to chain I was disconnected completely. As the current on chain I dropped, the current on chain III increased. In the first minute the input current to chain III was set to 10.5%. In the second minute, the current increment on chain III was already set to the standard 1.5% until minute 60, when the light source was already illuminating only through chain III.

The first 10% is a completely insignificant light source to the human eye and therefore does not need to be graduated and the control protocol is simplified. The dimming process of chain I was completed at minute 60, when chain I was completely de-energized and the illumination process of chain III was completed. The light source was on in this day mode through chain III the entire morning until full daylight, and before dusk the process was repeated in reverse order according to Example 13.

Example 15: Gradual Model of Dimming from Evening to Night of Exterior Luminaire The dimmer was controlled by a digital protocol to switch from daylight mode via chain III to nighttime mode via chain I. The switchover interval was set to 4 minutes. When, during the first minute after the start of the switching mode control, the input supply current to chain III was gradually reduced by 25% and the input supply current to chain I was gradually increased to 25% of its set point. During the second minute, the supply current to chain III was gradually reduced to 50% of the total and the supply current to chain I was further gradually increased to 50% of the total. During the third minute, the supply current to chain III was further reduced to 25% of the total and the supply current to chain I was further increased to 75% of the total. In the fourth minute, the value of the supply current to chain III was reduced to 0% and the supply current to chain I was further increased to 100% of the total. This process gradually switched the lighting modes from evening to night.

The switchover mode is preferably controlled based on an external signal either from the astrodyme or via a digital or analogue protocol to the dimming ballast or remotely manually.

Index overview:

| | |
|---|---|
| 1 | input in block of constant current source |
| 2 | input in block of power switches |
| 3 | chains |
| 4 | block of control circuit switches |
| 5 | output |
| 6 | blue LED with luminophore |
| 7 | amber LED |
| 8 | red LED |
| 9 | I. chain |
| 10 | II. chain |
| 11 | III. chain |
| V1 | varistor |
| R1 | protective resistor |
| D1 | rectifying circuit |
| D2, D3 | diode |
| D4 | Zener diode |
| C1, C2, C3, C4, C5, C6 | capacitor |
| R2, R3, R5, R6, R7, R8, R9, R10 | resistor |
| U1 | current source |
| U2 | control circuit |
| G | electrodes |
| T1 | transformer |
| Q1, Q2, Q3 | switch elements |
| D | terminals |

The invention claimed is:

1. An exterior luminaire comprising light-emitting diodes (LEDs) for emitting light under at least a daylight mode and a nightlight mode, with a circadian-adjustable light output mode for medical safety, comprising at least two switchable LED chips comprising a chain I and a chain III,
wherein the chain I comprises:
a first LED chip emitting orange light having a wavelength range of 580 nm to 610 nm, and
a second LED chip emitting red light having a wavelength range of 610 nm to 700 nm,
wherein the chain III comprises:
at least one blue LED chip overlaid with a luminophore emitting a continuous band spectrum of visible white light having a wavelength range of 440 nm to 700 nm and a correlated color temperature CCT of about 2200 to 4200 K,
wherein the chains I and III are each separately connected to a power source via a dimming ballast that regulates a proportion of an input current to each chain separately, such that switching between the chain I and the chain III is accomplished via a switching interval that is set for a period of at least 3 minutes, wherein the change in the input current occurs at a maximum rate of 25% per 1 minute, wherein the proportion of the input current to each chain changes by the value to one chain decreasing and the value to the other chain increasing;
wherein the daylight mode comprises emitting white light with the chain III energized and the chain I disconnected from the input current;
wherein the exterior luminaire switches from the daylight mode to nightlight mode by reducing the supply current to the chain III at a maximum rate of 25% by reducing the value of the supply current in one minute, wherein the reduction of the supply current to the chain III is in a single step or by a gradual decrease during the one minute, and
wherein simultaneously the value of the supply current to the chain I increases at a maximum rate of 25% during the one minute, resulting in a gradual, continuous, and unobservable transition between the daylight mode and the nightlight mode, and wherein the chain III is disconnected from the input current when the nightlight mode is engaged.

2. The exterior luminaire of claim 1, wherein switchover from the chain I to the chain III is set to at least 30 minutes, wherein the change in the input current occurs at a maximum rate of 2.5% per 1 minute.

3. The exterior luminaire of claim 1, wherein switchover from the chain I to the chain III is set to at least 60 minutes, wherein the change in the input current occurs at a maximum rate of 1.5% per 1 minute.

4. The exterior luminaire of claim 3, wherein the dimming ballast is controlled by software or via a protocol.

5. The exterior luminaire of claim 1, wherein the correlated color temperature CCT of the at least one blue LED chip is about 2500 to 2800 K.

6. The exterior luminaire of claim 1, wherein the color rendering index (CRI) of the emitted light has a value of at least 80.

* * * * *